(12) United States Patent
Fine

(10) Patent No.: US 10,606,059 B2
(45) Date of Patent: Mar. 31, 2020

(54) SAMPLE PROCESSING FOR MICROSCOPY

(71) Applicant: Alentic Microscience Inc., Halifax (CA)

(72) Inventor: Alan Marc Fine, Prospect (CA)

(73) Assignee: Alentic Microscience Inc., Halifax NS ( * ) Notice: Subject to any disclaimer, the term of this patent is extended or adjusted under 35 U.S.C. 154(b) by 0 days.

(21) Appl. No.: 16/404,633

(22) Filed: May 6, 2019

(65) Prior Publication Data

US 2019/0278075 A1  Sep. 12, 2019

Related U.S. Application Data

(63) Continuation of application No. 15/482,215, filed on Apr. 7, 2017, now Pat. No. 10,317,662.
(Continued)

(51) Int. Cl.
G02B 21/36 (2006.01)
G01N 21/49 (2006.01)
(Continued)

(52) U.S. Cl.
CPC ............ G02B 21/362 (2013.01); B01L 3/502 (2013.01); G01N 1/2813 (2013.01); G01N 1/38 (2013.01);
(Continued)

(58) Field of Classification Search
CPC .. G02B 21/361; G02B 21/34; G02B 21/0008; G01N 21/31; G01N 1/2813; G01N 1/38; G01N 2201/068; G01N 2201/12; G01N 33/492; G01N 2015/008; G01N 2015/0073; G01N 2015/0084; G01N 2015/1486; G01N 15/0612; G01N 2035/00079;
(Continued)

(56) References Cited

U.S. PATENT DOCUMENTS 6,084,683 A   7/2000 Bruno
6,180,314 B1  1/2001 Berndt
(Continued)

FOREIGN PATENT DOCUMENTS

JP  2000/002839   1/2000
JP  2007/532881   11/2007
(Continued)

OTHER PUBLICATIONS

U.S. Appl. No. 15/482,215, filed Apr. 7, 2017 U.S. Pat. No. 10,317,662 Issued.
(Continued)

Primary Examiner — Sang H Nguyen
(74) Attorney, Agent, or Firm — Fish & Richardson P.C.

(57) ABSTRACT

In some instances, an apparatus can include a light sensitive imaging sensor having a surface to receive a fluid sample, a body to be moved relative to the light sensitive imaging sensor and having a surface to touch a portion of the fluid sample, and a carrier to move the body toward the surface of the light sensitive imaging sensor to cause the surface of the body to touch the portion of the fluid sample, so that as the surface of the body touches the portion of the fluid, the surface of the body (i) is parallel to the surface of the light sensitive imaging sensor, and (ii) settles on top of the fluid sample independently of motion of the carrier.

37 Claims, 17 Drawing Sheets

Related U.S. Application Data

(60) Provisional application No. 62/320,120, filed on Apr. 8, 2016.

(51) Int. Cl.

| | | |
|---|---|---|
| *G01N 1/38* | (2006.01) | |
| *G01N 21/31* | (2006.01) | |
| *G01N 1/28* | (2006.01) | |
| *B01L 3/00* | (2006.01) | |
| *G01N 15/06* | (2006.01) | |
| *G02B 21/34* | (2006.01) | |
| *G02B 21/00* | (2006.01) | |
| *G01N 33/49* | (2006.01) | |
| *G01N 15/00* | (2006.01) | |
| *B01L 3/02* | (2006.01) | |
| *G01N 1/40* | (2006.01) | |
| *G01N 15/14* | (2006.01) | |
| *G01N 35/10* | (2006.01) | |
| *G01N 35/00* | (2006.01) | |

(52) U.S. Cl.
CPC ......... *G01N 15/0612* (2013.01); *G01N 21/31* (2013.01); *G01N 33/492* (2013.01); *G02B 21/0008* (2013.01); *G02B 21/34* (2013.01); *G02B 21/361* (2013.01); *B01L 3/0293* (2013.01); *B01L 2300/0663* (2013.01); *B01L 2300/0838* (2013.01); *B01L 2300/0858* (2013.01); *B01L 2300/0877* (2013.01); *G01N 2001/4083* (2013.01); *G01N 2015/008* (2013.01); *G01N 2015/0073* (2013.01); *G01N 2015/0084* (2013.01); *G01N 2015/1486* (2013.01); *G01N 2035/00079* (2013.01); *G01N 2035/1058* (2013.01); *G01N 2201/068* (2013.01); *G01N 2201/12* (2013.01)

(58) Field of Classification Search
CPC ..... B01L 2300/0663; B01L 2300/0838; B01L 2300/0858; B01L 2300/0877; B01L 2300/801
See application file for complete search history.

(56) References Cited

U.S. PATENT DOCUMENTS

| | | | | |
|---|---|---|---|---|
| 6,497,680 | B1* | 12/2002 | Holst | ............... A61M 5/14224 |
| | | | | 604/153 |
| 6,770,441 | B2* | 8/2004 | Dickinson | ............ B01J 19/0046 |
| | | | | 422/504 |
| 7,719,685 | B2 | 5/2010 | Li | |
| 7,850,916 | B2 | 12/2010 | Wardlaw | |
| 7,943,093 | B2* | 5/2011 | Adrien | .................... B01L 3/508 |
| | | | | 422/551 |
| 8,241,572 | B2 | 8/2012 | Wardlaw | |
| 8,506,909 | B2 | 8/2013 | Sunwold | |
| 8,906,325 | B2* | 12/2014 | Oldham | ................ B01L 3/5027 |
| | | | | 422/552 |
| 9,133,507 | B2 | 9/2015 | Testa | |
| 9,304,280 | B2 | 4/2016 | Gulari | |
| 10,317,662 | B2 | 6/2019 | Fine | |
| 2003/0201462 | A1 | 10/2003 | Pommer | |
| 2005/0190286 | A1 | 9/2005 | Kaduchak | |
| 2006/0197954 | A1 | 9/2006 | Ogura | |
| 2007/0148039 | A1 | 6/2007 | Padmanabhan | |
| 2007/0149863 | A1 | 6/2007 | Padmanabhan | |
| 2008/0144186 | A1* | 6/2008 | Feng | ....................... G02B 3/14 |
| | | | | 359/666 |
| 2008/0288179 | A1* | 11/2008 | Kao | ..................... B01L 3/5025 |
| | | | | 702/20 |
| 2010/0088039 | A1 | 4/2010 | Yang | |
| 2011/0014606 | A1 | 1/2011 | Steinmetzer | |
| 2011/0113901 | A1* | 5/2011 | Gonzalez | ............ B01F 11/0071 |
| | | | | 73/864 |
| 2011/0149280 | A1 | 6/2011 | Juhl | |
| 2011/0157344 | A1 | 6/2011 | Xie | |
| 2011/0164803 | A1 | 7/2011 | Wang | |
| 2011/0305842 | A1 | 12/2011 | Kram | |
| 2012/0218379 | A1 | 8/2012 | Ozcan | |
| 2012/0224053 | A1 | 9/2012 | Vykoukal | |
| 2012/0231533 | A1 | 9/2012 | Holl | |
| 2013/0010293 | A1 | 1/2013 | Okubo | |
| 2013/0040374 | A1 | 2/2013 | Tachibana | |
| 2013/0099143 | A1 | 4/2013 | Mogami | |
| 2013/0170730 | A1* | 7/2013 | Yu | ........................ G06T 7/0012 |
| | | | | 382/134 |
| 2013/0251592 | A1 | 9/2013 | McCaffrey | |
| 2014/0152801 | A1 | 6/2014 | Fine | |
| 2014/0300696 | A1 | 10/2014 | Ozcan | |
| 2014/0333926 | A1 | 11/2014 | Bond | |
| 2015/0002834 | A1 | 1/2015 | Fine | |
| 2015/0010205 | A1 | 1/2015 | Beijert | |
| 2015/0293012 | A1 | 10/2015 | Rapoport | |
| 2016/0056577 | A1 | 2/2016 | Hirose et al. | |
| 2017/0293133 | A1 | 10/2017 | Fine | |

FOREIGN PATENT DOCUMENTS

| | | |
|---|---|---|
| JP | 2016/507059 | 3/2016 |
| WO | WO 2014/205576 | 12/2014 |
| WO | WO 2015/089632 | 6/2015 |
| WO | WO 2017/173549 | 10/2017 |

OTHER PUBLICATIONS

U.S. Appl. No. 16/404,633, filed May 6, 2019 Pending.
International Search Report and Written Opinion from corresponding PCT application PCT/CA2017/050426 dated Jul. 25, 2017 (8 pages).
International Preliminary Report on Patentability from corresponding PCT application PCT/CA2017/050426 dated Oct. 18, 2018 (6 pages).
EP Extended European Search Report in European Application No. 17778522.7, dated Apr. 26, 2019, 8 pages.
USPTO Transaction History for U.S. Appl. No. 15/482,215, retrieved on May 8, 2019, 315 pages.
Japanese First Office Action in Japanese Application No. 2018-552780, dated Sep. 11, 2019, 10 pages with English Translation.
U.S. Appl. No. 15/482,215, filed Apr. 7, 2017 20170293133 Allowed.
USPTO Transaction History for U.S. Appl. No. 15/482,215, retrieved on Aug. 9, 2019, 315 pages.

* cited by examiner

SAMPLE PROCESSING FOR MICROSCOPY

RELATED APPLICATIONS

This application is a continuation and claims priority under 35 U.S.C. § 120 to U.S. patent application Ser. No. 15/482,215, filed Apr. 7, 2017, which claims priority under 35 U.S.C. § 120 to U.S. Provisional Patent Application No. 62/320,120, filed Apr. 8, 2016. This application is incorporated by reference here in its entirety.

This application relates to U.S. patent application Ser. No. 15/066,065, filed on Mar. 10, 2016; U.S. Pat. App. No. 62/131,164, filed on Mar. 10, 2015; U.S. patent application Ser. No. 14/314,743, filed on Jun. 24, 2015; U.S. Pat. App. No. 61/839,735, filed on Jun. 26, 2013; U.S. patent application Ser. No. 14/173,500, filed on Feb. 5, 2014; U.S. Pat. App. No. 61/255,781, filed Oct. 28, 2009; U.S. patent application Ser. No. 12/913,639, filed Oct. 27, 2010; U.S. patent application Ser. No. 13/095,175, filed Apr. 27, 2011; U.S. Pat. App. No. 61/761,467, filed Feb. 6, 2013; and U.S. Pat. App. No. 61/785,762, filed Mar. 14, 2013. These applications are incorporated by reference here in their entireties,

FIELD

This disclosure relates to sample processing for microscopy.

BACKGROUND

In a typical optical microscope, light passing through a sample is delivered to the eye of a user, a film, or a sensor through lenses, which then forms an image that is representative of the sample.

In other approaches, light representative of a sample can be detected and used to form an image of the sample without lenses by placing the sample on or near a detector, for example, an integrated circuit, that includes an arrangement of light sensitive elements. Signals generated by the detector can be processed to derive an image.

SUMMARY

In one aspect, an apparatus can include a light sensitive sensor configured to receive a fluid sample on top of a surface of the light sensitive sensor, a body configured to be moved relative to the light sensitive sensor, and a carrier device configured to move the surface of the body relative to the light sensitive sensor such that, when the surface of the body contacts the portion of the fluid sample, the surface of the body (i) is substantially parallel to the surface of the light sensitive sensor, and (ii) settles on the fluid sample independently of motion of the carrier.

In some implementations, the body permits passage of light onto the light sensitive imaging sensor.

In some implementations, the surface of the light sensitive imaging sensor to receive the fluid sample includes a hydrophilic coating.

In some implementations, the surface of the body to touch a portion of the fluid sample includes a hydrophilic coating.

In some implementations, the apparatus further includes comprising a sample delivery component for preparing and delivering the fluid sample to the surface of the light sensitive imaging sensor. In some instances, the sample delivery component includes at least two volumetric capillary tubes, a nozzle for mixing fluids within the at least two volumetric capillary tubes, and an output tip through which the fluid sample is delivered to the surface of the light sensitive imaging sensor.

In some implementations, the body includes an extension that lies on the carrier. In some instances, the extension of the body has features that match corresponding features on the carrier.

In some implementations, the apparatus further includes device that causes an adjustment to the a vertical distance between a bottom surface of the carrier and the surface of the light sensitive imaging sensor that receives the sample fluid.

In another aspect, a method may include moving a body toward a fluid sample that is on a surface of a light sensitive imaging sensor so that as a surface of the body touches the fluid sample, the surface of the body is parallel to the surface of the light sensitive imaging sensor and the body settles on the fluid sample.

In some implementations, moving the body toward the fluid sample includes placing the body on a carrier such that the center of the body is vertically aligned with the center of the light sensitive imaging sensor.

In some implementations, moving the body toward the fluid sample includes moving the carrier toward the fluid sample.

In another aspect, an apparatus includes: a solid member; a light sensitive imaging sensor; a deformable member coupling the solid member and a surface including the light sensitive imaging sensor, the deformable member comprising side walls enclosing a fluid chamber configured to receive a volume of fluid, a surface of the fluid chamber comprising the light sensitive chamber; and a component that deforms the deformable member to cause adjustment to a height of the fluid chamber.

In some implementations, the solid member permits passage of light into the fluid chamber.

In some implementations, the component that deforms the deformable member includes a transparent-roofed pressurizable chamber enclosing the fluid chamber.

In some implementations, the base includes an integrated circuit board.

In another aspect, a method includes: injecting a fluid sample into a chamber; deforming a deformable member to reduce a volume of the chamber to cause a reduction of volume of the sample; and after reducing the volume of the sample, capturing an image of the portion of the sample at a light-sensitive sensor surface within the chamber.

In some implementations, the method includes deforming the deformable member to increase the volume of the chamber.

In some implementations, deforming the deformable member to reduce the volume of the chamber includes withdrawing a volume of gas within an expandable chamber within the chamber.

In another aspect, a point-of-care apparatus includes: a sample processing chamber including a base having a chamber and a light sensitive sensor having a surface within the chamber to receive a fluid sample, and a body to be moved relative to the light sensitive imaging sensor and having a surface to touch a portion of the fluid sample so that as the surface of the body touches the portion of the fluid, the surface of the body (i) is parallel to the surface of the light sensitive imaging sensor, and (ii) settles on the fluid sample; a device coupler to couple electronically to a mobile device capable of accepting electronic communications corresponding to signals derived from the light sensitive imaging sensors; and a housing to hold the sample processing chamber and the device coupler.

In some implementations, the surface of the light sensitive imaging sensor to receive the fluid sample includes a hydrophilic coating.

In some implementations, the point-of-care apparatus includes a sample delivery component for preparing and delivering the fluid sample to the surface of the light sensitive imaging sensor.

In some implementations, the sample delivery component includes at least two volumetric capillary tubes, a nozzle for mixing fluids within the at least two volumetric capillary tubes, and an output tip through which the fluid sample is delivered to the surface of the light sensitive imaging sensor.

In some implementations, the surface of the body to touch the portion of the fluid sample is on a component that is separable from the body.

In some implementations, the component that is separable from the body includes a plate and a protruding element that is lowered into the recessed chamber of the base.

In some implementations, the dimensions of a top surface of the protruding element are identical to dimensions of the surface to touch the portion of the fluid sample, and the top surface of the protruding element is the surface of the body to touch the portion of the fluid sample.

In some implementations, the shape of the protruding element is includes a truncated pyramid.

In some implementations, the electronic communications exchanged between the mobile device and the light sensitive imaging sensor include an instruction to capture an image of a portion of the fluid sample placed on the surface to receive the fluid sample Unless otherwise defined, all technical and scientific terms used here have the same meaning as commonly understood by one of ordinary skill in the art to which this invention belongs. Although methods and materials similar or equivalent to those described here can be used in the practice or testing of the present invention, suitable methods and materials are described below. All publications, patent applications, patents, and other references mentioned here are incorporated by reference in their entirety. In case of conflict, the present specification, including definitions, will control. In addition, the materials, methods, and examples are illustrative only and not intended to be limiting.

The details of one or more implementations are set forth in the accompanying drawings and the description below. Other potential features and advantages will become apparent from the description, the drawings, and the claims.

DETAILED DESCRIPTION

Figure 1:
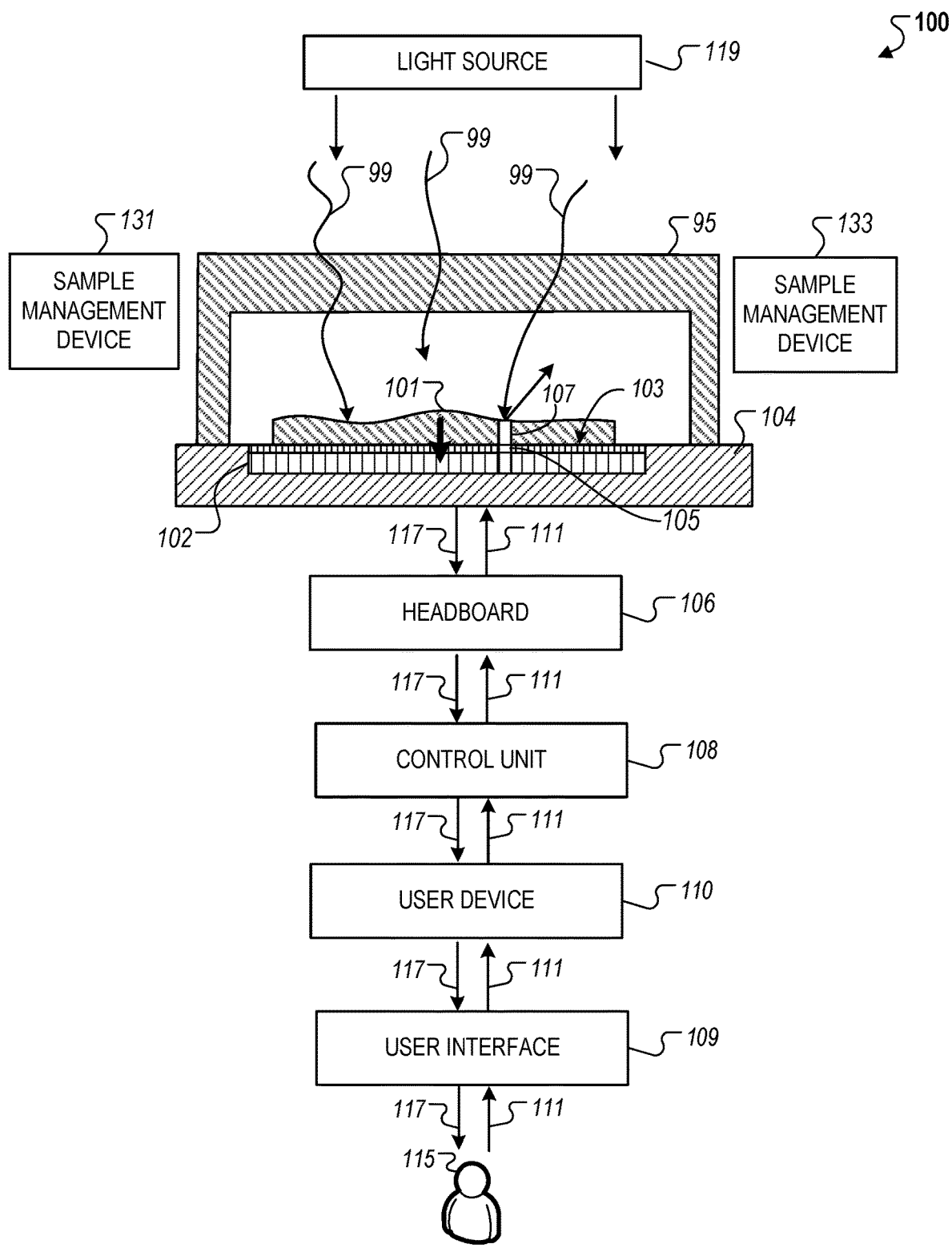
FIG. 1 is a schematic diagram that illustrates an example of a contact microscopy system.

Images captured using contact microscopy often require a well-defined surface of contact between a light sensitive sensor surface and particles to be analyzed. For quantitative techniques the ability to compute an accurate particle count within a fluid sample is based on forming a thin layer of uniformly distributed sample over the sensor surface where the height of the thin layer is roughly the diameter of the particles (for example, a monolayer). However, due to a variety of complexities within micro-environments (e.g., fluid-surface interactions, lack of sufficient precision in adjusting the placement of physical components), establishing and maintaining the layer of uniformly distributed sample prior to conducting an imaging procedure is often difficult, complicating efforts to repeat accurately the use of similar techniques in subsequent imaging procedures.

One field where contact microscopy techniques can be applied is for performing blood counts where cells or cellular components such as red blood cells and platelets are counted in a carefully controlled volume of blood. Blood counts can be useful in diagnosing pathologies and health conditions, determining severities associated with such diagnoses, and monitoring changes in diseased conditions of patients.

However, while such technologies are ubiquitous in the health care systems of developed countries, their application has been limited in the developing world. For instance, blood counts can be expensive to administer, and tend to be performed on dedicated machines operated in dedicated labs, for example, in hospitals or clinics, which hampers their use in resource-limited or remote locations where the lack of skilled operators often preclude the use of large-scale technologies with a relatively high complexity.

Accordingly, innovative aspects described throughout this specification relate to improving sample processing for contact microscopy techniques used to compute blood counts, among other applications. The systems and techniques described here provide a cost-effective means to improve the repeatability and accuracy of performing blood counts. For instance, structures of the systems can be designed to enhance techniques that are directed to establishing and maintaining a uniformly distributed thin sample layer over a sensor surface to consistently compute a cell count. The figures and elements shown in them are not always to scale and many of them are illustrated schematically. The spatial relationships of the elements in the figure may appear differently than the descriptions in the text, for example, above and below and top and bottom may be shown oppositely in the figures from the way they are described in the text.

As described here, "light sensitive locations" include, for example, any features of a device that are separately sensitive to light or separately capable of emitting light, or both, including light sensitive elements or pixels and light source locations. The phrase light source locations can refer to elements capable of emitting light. In some cases, the phrase light sensitive location can refer to an exposed light sensitive portion of a feature of the device without any covering, protective layer, shield, or any other feature that might separate the light sensitive from the ambient or from a sample.

As described here, "contact microscope" or "contact microscopy" refers to any imaging device or technique that includes a light-sensitive sensor in contact with a sample to be image. For example, a contract microscope may include: (a) a high resolution sensor of closely spaced light sensitive or a high resolution set of light emitting locations that are exposed to the ambient at a surface of the device together with (b) a device to associate with that surface a portion of a sample that is to be imaged, and, in the case of light emitting locations, a light detector relatively far from the light emitting locations and sample, so that the portion of the sample is in contact with (or nearly in contact with) the surface and a usable high resolution image can be obtained by the sensor when the portion of the sample is in place.

As described here, a "sensor" refers to an integrated circuit, or a component of an integrated circuit that includes a light-sensitive element. For example, a sensor can be a component that receives light at the light sensitive elements and generates signals or data representing the intensities of light detected by the light sensitive elements, and processes any electronic elements that directly drive the light sensitive elements or cause the light-generated signals or data to be delivered by the light sensitive elements.

As described here, "parallel" arrangement of surfaces may include a substantially parallel arrangement between a chamber top and a surface of the light sensitive sensor such that the arrangement provides a uniform distributed of particles over the surface of light sensitive sensor.

As described here, "settling" refers to placement of a surface of a body over a sample such that the body stably sinks towards the top the sample. For instance, a body can settle on top of a sample if, for example, the body is not attached to, or held in place by, a separate component. In other instances, the surface of the body may settle on top of the sample based on the body being pressed against the sample.

System Overview In contact microscopy, a sample to be analyzed is associated with light-sensitive features of a sensor in that it is, for example, in direct contact (e.g., without any intervening materials) with the light sensitive features of a sensor or the light imaging of the light source, or nearly in contact with the light sensitive or emitting features. For instance, "nearly in contact" can refer to, for example, within the near field of the light sensitive or light emitting features, which in some instances refers to being at a distance that is within ½ of the wavelength of the light involved or possibly at a distance that is within a range of wavelengths of the light involved.

In embodiments of the system and techniques that we describe here, a device or devices can be used to associate the sample with the sensor surface. Such an association can include any mechanism that facilitates the movement, flow, delivery, placement, or presentation, for example, of a portion of the sample into contact with or nearly into contact with the light sensitive locations, including any mechanism that uses mechanical, electrical, electromechanical, pneumatic, hydraulic, capillarity, surface wetting- and gravitational forces, among others.

A. System Components

FIG. 1 illustrates an example of a system 100 that generally includes various components used to capture high-resolution images of a sample 101 that is in contact with, or in close proximity to, a surface 103 of a light sensor 102. The system 100 also includes a light source 119, sample management devices 131 and 133, an integrated chip 104, a headboard 106, a control unit 108, a user device 110, and a user interface 109.

The light sensor 102 includes a two-dimensional arrangement of light sensitive elements 105 that can correspond to an array of pixels in the captured images. For simplicity, the elements of the light sensor 102 are described here as "pixels." High resolution images can be captured using various color schemes (e.g., full-color, gray-scale, black-and-white) or a combination of color schemes. In addition, the sample 101 can be in various phases (e.g., gas phase, liquid phase, solid phase), or a combination of such phases or other phases.

The light sensor 102 can also include other components, either as part of, or in addition to, the light sensitive elements 105 that perform various functions. For instance, the components can drive or read sensing elements and generate, process, and deliver electronic signals to the other components of the system 100 (e.g., headboard 106, control unit 108, user device 110). The components of the light sensor 102 can also perform other functions such as receiving data transmissions from the components of the system 100.

The sensor 102 can be a component of or formed on the integrated circuit chip 104, which can be made in a homogeneous fabrication mode, a hybrid fabrication mode, or other conventional fabrication techniques. The chip 104 can be mounted on the headboard 106, which can be part of or be connected to the control unit 108.

The control unit 108 can be part of, or connected to, the user device 110. The user device 110 can provide the user interface 109 for access by a user 115 to adjust and control the operations of the system 100. For instance, the user device 110 can receive information 111 (e.g., commands) through the user interface 109 from the user 115, process the received information 111, and transmit the received information 111 to the control unit 108. In addition, the control unit 108 can receive data 117 (e.g., sensor data from the light sensor 102) from the headboard 106, process the received data 117, and transmit the received data 117 to user device 110 for display on the user interface 109. In some instances, the user interface 109 can operate through the control unit 108 or the headboard 106, or a combination of the various components of the system 100.

The light source 119 can either be an external light source outside the system 100 (e.g., a room light) that provides ambient light for imaging, or a dedicated light source that provides specific illumination and intensity control of the light provided over the sample 101. For instance, the light source 119 can be controlled, either by the user device 110, or the control unit 110, to adjust the intensity, focus, position, orientation, uniformity of illumination and/or other optical properties of the light provided over the sample 101.

Since the sample 101 is in contact with or in close proximity to the surface 103 of the light sensor 102, additional optical elements are not necessary to refract, collimate or redirect the light towards the light sensors 102 for imaging. For instance, light 99 from a portion 107 of the sample that is adjacent to a pixel (or is in a path between the incident light 99 and the pixel) will be received largely (in some cases essentially entirely) by that pixel 105. In this arrangement, the light 99 sensed by the array of pixels of the light sensor 102 is directly representative of a corresponding array of portions of the sample 101 and therefore represents, in effect, a high resolution image of the sample 101.

The sample transport and management devices 131, 133 can include mechanical or electrical components, or combinations of such, that assist in loading and delivery of the sample 101 to a location on the surface 103 of the sensor 102 for image capture and to the formation of a thin uniform layer, such as a monolayer, a sample on the surface. For instance, the devices 131, 133 can be used to move a container including the sample 101 horizontally or vertically along the surface 103 to position the sample 101 in an optical location over the sensor 102 and hold the container at the optical location during an imaging procedure. The devices 131, 133, can also process the sample before and after the imaging procedure. For example, devices 131, 133 can be used to mix chemical reagents with the sample 101 during sample preparation, remove chemical reagents from the sample 101 for purification, fetch the sample 101 from an external source, dispose of an imaged sample after an imaging procedure, or any other function that may be used with respect to the sample 101 for an imaging procedure.

The user device 110 can be any type of electronic device that is capable of generating a user interface for receiving and transmitting data communications. For instance, the user device 110 can be a handheld device such a cell phone, a tablet computing device, or a laptop computing device, or a stationary device such as a desktop computer, or a work station. In some instances, the user device 110 can also be any type of instrument that is used by the user 115 to adjust the function of the control unit 108.

As described more particularly below, the system 100 also includes a chamber top 95 (or "lid," "cover" or "chamber wall" as described here) that can abut, touch, surround, or enclose a chamber, adjacent to an exposed surface 103 of the light sensor 102 that holds a portion of the sample 101. Specific descriptions related to the use of the chamber top 95 in relation to the operation of the system 100 are provided below. In some implementations, the chamber top 95 can be configured to be able to be lowered to contact the sample 101 and adjust the volume of the sample 101 (e.g., the volume as determined by the area of the sensor and the thickness of the sample layer atop the surface 103 of the light sensor 102). As an example, the adjustment can be done by lowering the bottom surface of the chamber top 95 against the sample 101 such that the excessive amount of the sample 101 flows out horizontally along the surface 103 of the light sensor 102. The chamber top 95 can also descend in other manners as described more particularly below. As described here, the space formed between the bottom surface of the chamber top 95 and the surface 103 of the light sensor 102 once the descent of the chamber top 05 is complete forms a "chamber" for the sample 101. Thus, the volume of the sample 101 that is initially placed on top of the surface 103 is greater than the volume of the sample 101 within the chamber since, after the chamber top 95 initially comes into contact with the sample 101 and before the chamber top 95 reaches its final placement, excess volume of the sample 101 (e.g., the difference between the sample 101 volume introduced and the volume of the chamber) is removed from the chamber as portion of the sample 101 flows out of the chamber. In some instances, the excess volume of the sample 101 flows out laterally to the surface 103. In other instances, the bottom surface of the chamber top 95 can be porous surface, which enables the excess volume of the sample 101 to flow out of the chamber through the pores of the chamber top 95. In these instances, the pores may be sized such that only fluid passes through the pores but particulate matter of the sample 101 are too large to pass through the pores.

Although FIG. 1 illustrates various components of the system 100, a commercial product associated with the system 100 need not include each of the components depicted in FIG. 1 and described here (and may include components other than those shown in the figure). In various implementations, any combination of two or more of the light sensor 102, the chip 104, the headboard 106, the control unit 108, and the user device 110 can have a variety of mechanical and electrical connections among them. In addition, mechanical, fluid flow, electronic, software, data processing, communication, storage, and electrical functions needed for various operations can be distributed in a variety of ways between and among pairs and three or more of those parts of the system. The distribution of functions can either be arbitrary or based on commercial and technological considerations in a wide variety of ways.

B. System Operation

During operation, the light sensor 102 detects incident electromagnetic radiation 99 (or "light") that is generated from the light source 119 and is scattered from, or emanates from the sample 101. Light that passes through, scattered from, or emanates from the sample 101 may be altered in wavelength, for example, as it passes through or is scattered or emanates. The incident light 99 and the transmitted, scattered, or emanated radiation is typically in the wavelength range of visible light, near ultraviolet, or near infrared. As described here, however, the light 99 can include light from all such ranges.

To capture an image of the sample, the light sensor 102 is driven and read during an image capture cycle. During an image capture cycle, the light 99 received by the light sensor 102 at each of its pixels is converted to electrical signals (e.g., analog signals or digital values) that are delivered to electronic components of the chip 104. The signals may be read in parallel or serially depending on the components of the chip 104. The electrical signal from each of the pixels is typically represented by a quantized intensity value corresponding to the intensity of light sensed by the pixel, within some range such as a range represented by, e.g., 16 bit digital values.

Color information can be obtained in a variety of ways, for example, using band-pass optical filters over multiple adjacent pixels, or sequential imaging with different color illumination, among others. The electrical signals that are received from the various spatial pixels can represent a full-color high-resolution high-dynamic range image of the sample 101. In addition to the electronic features of the system 100, there are mechanical elements discussed below that among other things handle, contain, and illuminate the sample 101.

Sample Preparation

A. Sample Characteristics

The sample 101 (also referred to as "specimen" interchangeably) can be in any type of phase (e.g., liquid, solid, gas) or combination of such that is in direct contact with the surface 103 of the light sensor 102. In some instances, the sample 101 is a fluid that includes various types of particulate matter such as cells (e.g., human or animal blood cells, mammalian cells, bacterial cells, and/or plant cells), molecules (e.g., DNA, RNA, peptides), proteins (e.g., antigens and antibodies), or contaminants in environmental or industrial sample. In such instances, the sample 101 can be dispensed into a chamber above the surface 103 and manipulated using the devices 131, 133 to position the sample 101 over the light sensor 102.

Figure 2:
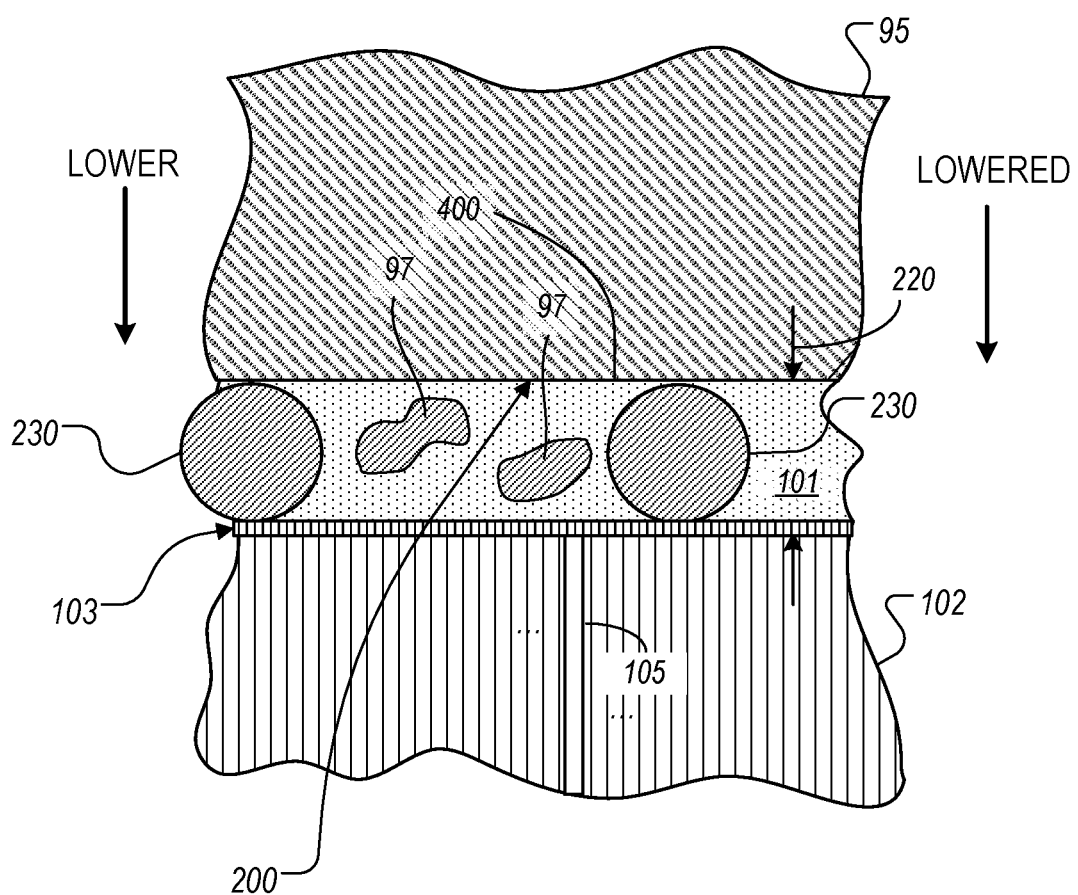
FIG. 2 is a cross-sectional diagram that illustrates an example of lowering a chamber top onto a sensor surface of a contact microscopy system.

Referring to FIG. 2, the sample 101 that is being imaged can be composed of or include small similar types of units 97, such as particles, bits, specks, cells, or molecules, or combinations of them or combinations of any two or more of the different types. The units 97 may be suspended in or carried in a liquid 101 to form liquid-suspended particles 97, entrained in a gas to form gas-suspended particles 97 (not shown), rest in an unsuspended and un-entrained form (e.g., a powder) on the surface 103 of the light sensor 102 (not shown), or be held in an integrated matrix of solid, gelled, or other integral self-supporting material such as a sectioned layer of tissue, among others. As described here, "matrix" can include, for example, any material in which particles 97 are held, including liquid, gas, solid, gel, or other materials.

Sample Delivery

A. Dispensing Technique

Figure 4A:
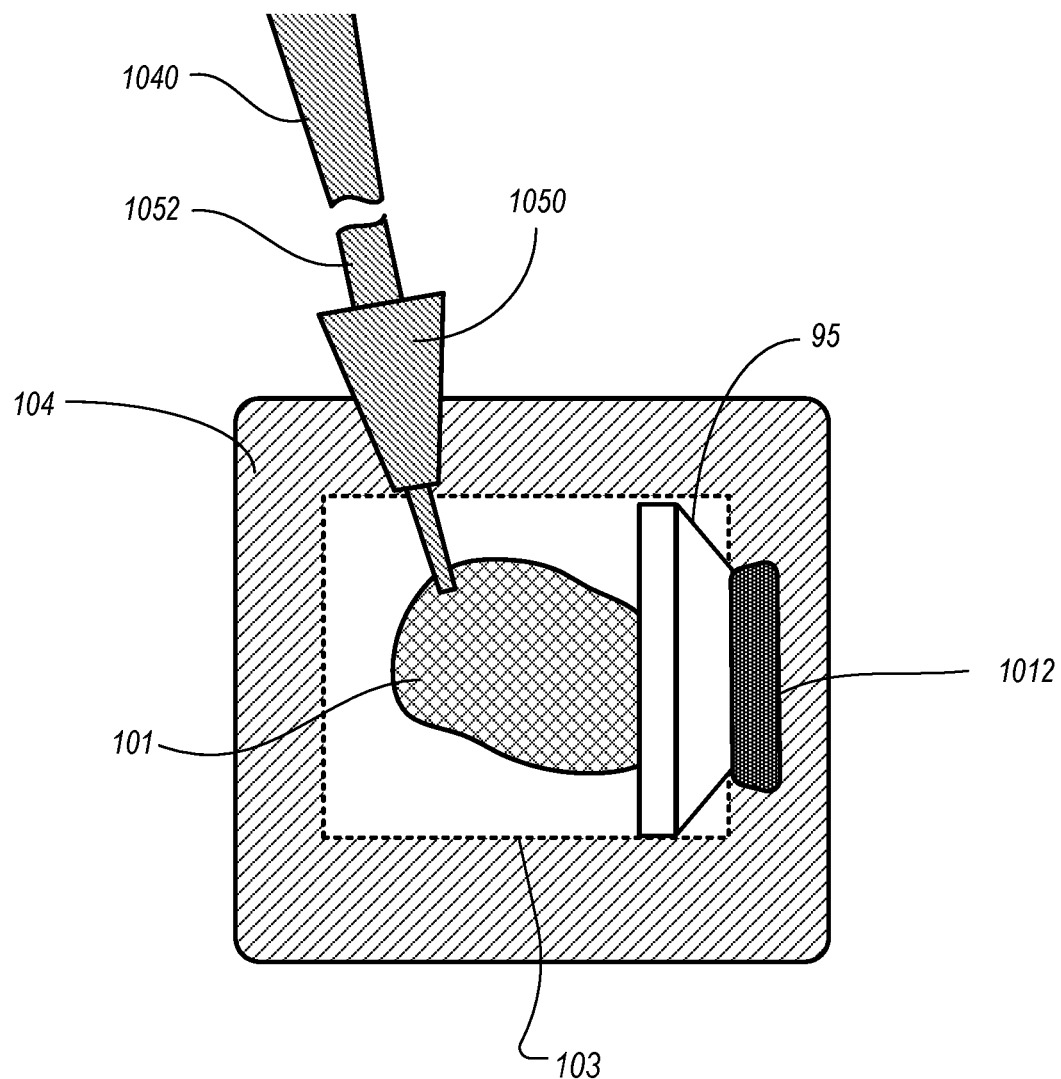
FIGS. 4A-4C are schematic diagrams that illustrate techniques and components used to dispense a sample onto a sensor surface.

FIG. 4A illustrates, for some embodiments of the system and techniques described here, a top view of the system 100 during a sample dispensing procedure. As depicted, a predetermined volume of the sample 101 is dispensed onto the surface 103 of the light sensor 102 prior to performing an imaging procedure. The volume of the sample 101 is dispensed using a fluid-loading pipette 1040 using a guide 1050 to bring the pipette tip 1052 close to a predetermined position such that the sample 101 is deposited on top of the surface 103.

As described more particularly below, various types of dispensing techniques can be used to deliver the volume of the sample 101 onto the surface 103. In some instances, the fluid-loading pipette 1040 is a specific type of pipette referred to here as a "duplex pipette." In some instances, the fluid-loading pipette 140 is a conventional micropipette.

In some implementations, the chamber top 95 and/or the surface 103 of the sensor 102 is coated with hydrophilic coatings to enhance the capillary force and increase the speed of the sample delivery process. In some implementations, hydrophobic coatings can be used surrounding the sensor active area to contain liquid specimen. In situations when settling of the particles 97 is an important concern, the sample 101 can be mixed, e.g., during fluid ejection and/or the chamber top 95 descent, either or both of which can be automatically controlled, with the use of pumps, actuators, among other techniques.

B. Duplex Pipette

Figure 4B:
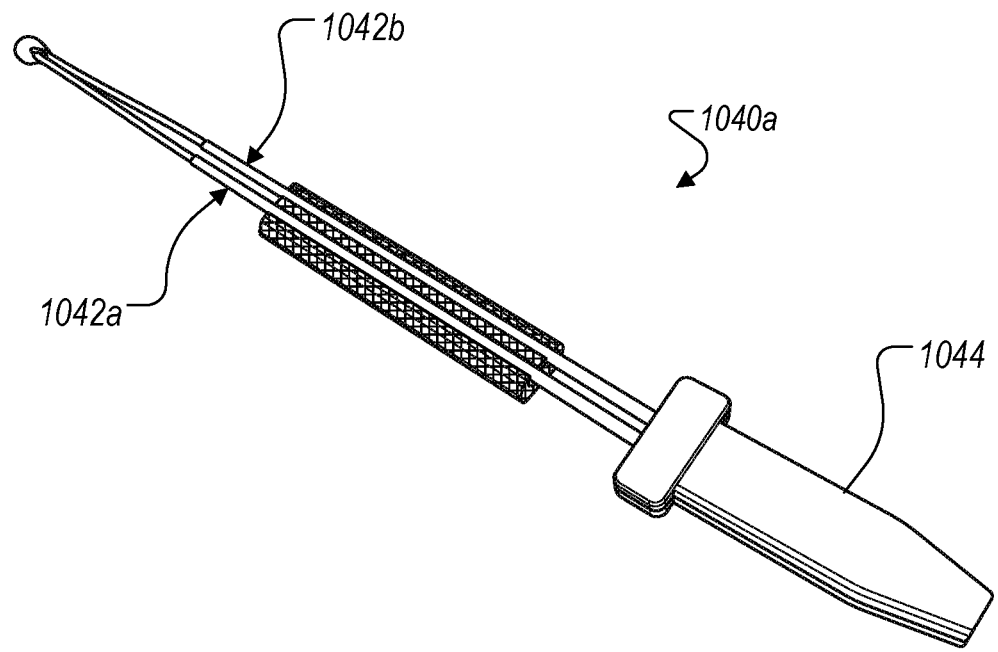
Figure 4C:
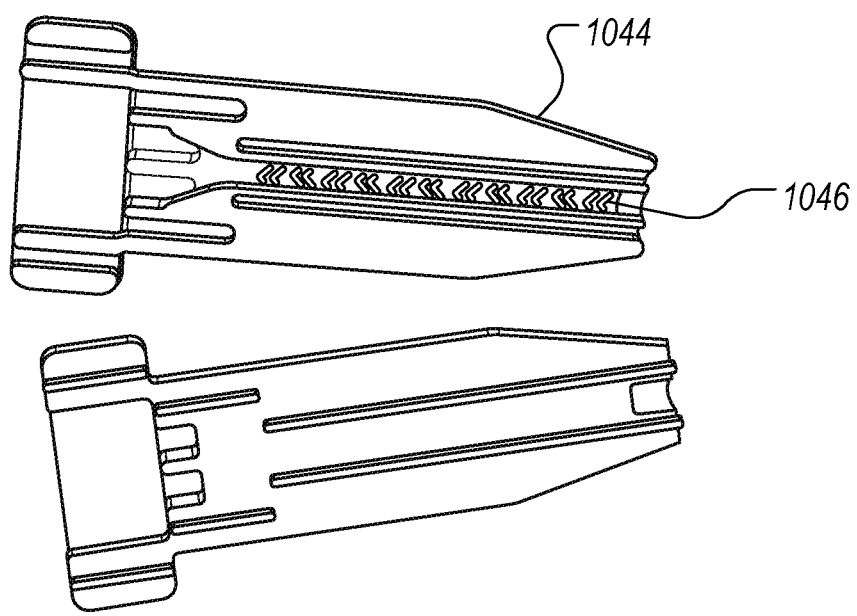

FIGS. 4B and 4C illustrate schematic diagrams of examples of the fluid-loading pipette 1040a that are referred here as duplex pipette 1040a. Referring to FIG. 4B, the duplex pipette 1040a includes two volumetric capillary tubes 1042a and 1042b that deliver separate input fluid streams (e.g., blood sample and diluent/chemical stain) to a mix-well chamber 1044, which combines the two input fluid steams into a mix-well chamber 1044 with an aperture at other end for dispensing the mixed fluid of the two input fluid streams.

FIG. 4C illustrates the internal structure of the mix-well chamber 1044. As depicted, the left portion of the mix-well chamber 1044 includes two receiving ports where ends of the volumetric capillary tubes 1042a-b are attached to the mix-well chamber 1044. The mix-well chamber can in some embodiments be detachable from the fluid containers 1042a-b such that a single mix-well chamber 1044 can be reusable for multiple deliveries of a single sample 101. The two receiving ports converge into a single channel that includes grooves 1046 to help combine the two input fluid streams into a single output. For example, the grooves 1046 can be arranged transverse to the fluid flow through the fluid channel such that the grooves 1046 disturb fluid flow and enhance combination of the two input fluid streams as previously described in scientific literature.[1]

[1] Sabotin, I., Tristo, G., Bissacco, G., Junkar, M., & Valentincic, J. (n.d). Staggered Herringbone Mixer designed for micro EDM milling. Retrieved Jul. 7, 2015, from http://lab.fs.uni-lj.si/at/uploads/edm/bibJoze/10-imbt.pdf C. Spacing Features A wide variety of techniques and devices can be used to form and maintain a height (e.g., a precise height) of the gap 220. As described here, such techniques are generally referred to as "spacing features." In the example shown in FIG. 2, the spacing feature includes microspheres or other kinds of beads of uniform size. As an example, in some implementations, the spacing features 230 are monodispersed rigid polymeric microspheres with a precisely defined diameter (e.g., 3.00 μm with a less than five percent coefficient of variation). In this example, to establish a precise and uniform spacing of the gap 220, which relates to the volume of the sample 101 between the chamber top 95 and the surface 103, the precision of the bead sizes can be used to ensure that gap 220 is repeatable in multiple imaging procedures.

In some instances, for a given kind of sample unit or a precisely specified volume of sample (e.g., for a blood count, or other analysis in which the number of particles 97 is to be counted for a precise volume of the sample), the volume of the sample 101 to be imaged is precisely controlled by the width and length of the top surface of the light sensor 102 and by the height of the gap 220 (or the chamber) between the surface 102 and the flat bottom surface of the chamber top 95. In some instances, the volume may not need to be precise, but the gap height may need to be a precise amount, or no larger than a certain amount, or no smaller than a certain amount, or a combination of those conditions.

As shown in FIG. 2, in some implementations, the spacing features 230 are included within the sample, for example, a sample having a liquid matrix in which is particles 97 (which may be smaller than the beads) are suspended, when the sample is delivered to the sensor surface 103. If the chamber top is then allowed to settle on or be pressed down onto the sample, and assuming that there are enough beads in the sample and they are reasonably well distributed within the liquid, then a uniform accurate gap height can be achieved. For this purpose, the beads might be present in the sample at the rate of 10,000-500,000 beads per microliter of sample, for example. Maintaining an even distribution of the beads in the sample can be done by simple mechanical agitation if the beads are selected to have close to neutral buoyancy in the sample.

In some cases, the beads can be roughly the same size as the particles 97. In some implementations, beads of two different sizes can be included. A larger size defines the intended spacing. A smaller size can be counted to verify that the volume of the sample space is as intended, assuming the smaller beads are distributed through the sample reasonably uniformly, and the number of smaller beads per unit volume of the sample is known. The beads may be transparent in order to allow light to pass through to the sensor, or may be colored, or fluorescent, or opaque, or a combination of two or more of those characteristics.

In some implementations, instead of using spacing features 230 that are included within the sample 101, the height of the chamber (e.g., the gap 220) formed between the bottom surface of the chamber top 95 and surface 103 can instead by maintained by a set of array of pillars that protrude from the surrounding surface around the surface 103 (e.g., on the surface of the headboard 106). In such implementations, the headboard 106 that houses the surface 103 can be specifically fabricated such that the pillars have a predetermined height corresponding the optical gap 220 required for a particular imaging procedure. In operation, after introduction of the sample 101, the chamber top 95 can then be lowered onto the surface 103 until the bottom surface of the chamber top 95 comes into contact with the top surface of the pillars. Various aspects of the pillar array (e.g., array pattern, pillar density) can also be adjusted to impact the distribution of particles 97 along the surface 103.

In some instances, the amount of sample 101 loaded onto the light sensor 102 is larger than the amounted necessary for imaging. In some implementations, the sample 101 needs to be in the form of a relatively thin layer, (e.g., 1 µm to 100µ), or have a thickness such that a single layer of cells of the sample is displaced on the sensor for imaging. In such instance, a chamber top 95 can be descended to contact the sample 101 and adjust the volume of the sample 101 (e.g., the thickness of the sample layer atop the surface 103 of the light sensor 102.

D. Post-Dispensing Sedimentation

As described here, it may be desirable that the concentration of the sample 101 to be imaged is either the same as, or has a predetermined relationship to, the bulk concentration of the sample that is initially dispensed on the surface 103. In some instances, weight of the particulate matter within the sample 101 (e.g., the particles 97 and the spacing features 230) are heavier than the other fluidic components of the sample (e.g., diluent), which makes the particulate matter susceptible to accumulation as opposed to flowing or moving when an force is applied to a volume of the sample 101.

One example of an external force may be gravity, which can cause sedimentation concentration gradients in the sample 101 as the particles 97 descend toward the bottom of the sample 101 due to a gravitational force. Another example of a force can be the force applied by the bottom surface of the chamber top 95 during the descent of the chamber top 95 as described here. In this example, the chamber top 95 accelerates downward, the sample 101 outside the perimeter of the sensor 102, and the heavier suspended particles 97 have more momentum than the fluidic components and may not move or accelerate as quickly as the other parts of the sample 101. In such an instance, the particles 97 may be left on the surface 103 of the light sensor 102, leading to a higher concentration than the bulk concentration in the sample 101 dispensed on the surface 103 before the excessive volume of the sample 101 is removed. In yet another example, the force may also include friction force between the sample 101 and the various surfaces of the system (e.g., the surface 103, the surface 1006, etc.) or a shear force generated within the sample as a result of interactions with such surfaces. The friction force and the shear force may reduce the speed of the particles 97 relative to the sample flow.

Additionally, after the chamber top completes its descent, the sample may continue to flow, causing the particles 97 to move and disrupting their imaging. In some implementations, the viscosity of the sample may be adjusted to control the concentration of the particles 97 and reduce the flow of the sample during imaging. In some examples, the adjustment can be done by adding one or more viscosity-controlling agents to the sample. The sedimentation rates of the particles 97 can be reduced and the fluid can be allowed to exert a stronger force on the spacer beads and the particles 97 to counter their momentum and friction. The increased viscosity also can reduce the likelihood of flow after the chamber top completes its descent. Suitable agents can include dextran, glycerol, starch, cellulose derivatives such as methyl cellulose, any combination of these materials, and other materials.

Alternatively or additionally, one or more agents can be added to the sample to increase diluent density so that the difference in density between the diluent and the spacer beads and/or the particles 97 is reduced or even eliminated. The reduced or eliminated density difference can also control the concentration of the particles 97 and reduce the flow of the sample during imaging.

The agent for increasing the diluent density can be the same agent as the viscosity-controlling agent. In some implementations, thixotropic agents can be used to achieve the same effects, and also allow for easier mixing of the particles 97 with the diluent. In some situations, photo-cross-linkable agent(s) or gelling agent(s) (e.g., temperature dependent, such as low-melting-point agarose) can be used to increase the sample viscosity while allowing for easy mixing of the particles 97 and the diluent. For example, a sample with suspended particles 97 and a gelling agent such as liquid agarose may initially be squeezed by the chamber top 95 to form a monolayer of particles 97 on the surface 103. The temperature of the sample can be cooled to form an agarose gel structure that "traps" the particles 97 in their position within the monolayer, which can then be used, e.g., to perform a comet assay of DNA damage. For instance, to perform a comet assay, the sample may include a DNA-intercalating stain for detecting particles 97 that may be cancerous cells. In such instances, after gelling, the chamber top can be briefly raised permitting a cell lysis media to permeate the gel; a voltage gradient may subsequently be generated along the length or width of the chamber by electrodes that may also be placed on opposite ends of the chamber (e.g., on two opposite sides of the chamber top 95 running down to opposite edges of the truncated top surface 1102 of the chamber top). In other instances, polyacrylamide, starch, or other gels may be used to enable rapid, inexpensive electrophoresis analysis of proteins, nucleic asides and other macromolecules. The electric field produced by the electrodes can be used to induce movements of small particles in suspension (e.g., not trapped within the gel), and such movement may be monitored using the image sensor 102 to measure either surface charge or zeta potential of the particles 97.

Chamber Top Descent

E. Lowering Techniques

Once the sample 101 has been dispensed on the surface 103 of the light sensor 102, the chamber top 95 can be lowered towards to the surface 103 to remove excessive volume of sample 101 atop the surface 103 to generate a thin layer of the particles 97 (e.g., cells that are disbursed in a fluid sample) to be evenly distributed over the surface 103. In some implementations, the removal of the excessive volume is performed in such a manner that the displacement of the excess volume does not alter the bulk concentration of the particles 97 above the surface 103 of the light sensor 102 so that the relatively small volume of the sample 101 (e.g., about 40 nL) that is imaged is representative of the bulk sample (e.g., about 50 µL or more) dispensed onto the surface 103 of the light sensor 102. In other implementations, the removal process generates a new concentration of particles 97 within the relatively small volume sample of the sample 101 that is consistently proportional to the bulk concentration of the particles 97. In such implementations, a correction factor can be determined and applied to the captured data to derive the desired sample concentration for imaging. For instance, to achieve the desired sample concentration for imaging, the sample 101 can be further processed using techniques described further below.

Figure 3A:
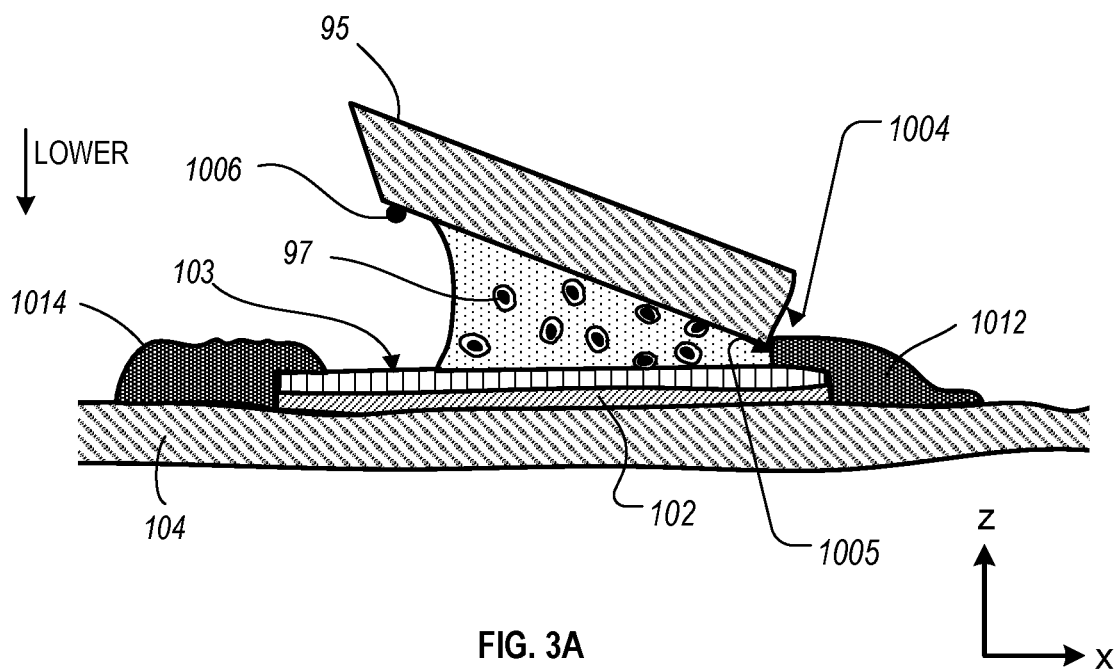
FIGS. 3A-3B are schematic diagrams that illustrate examples of a contact microscopy system where a chamber top is lowered along one side.
Figure 3B:
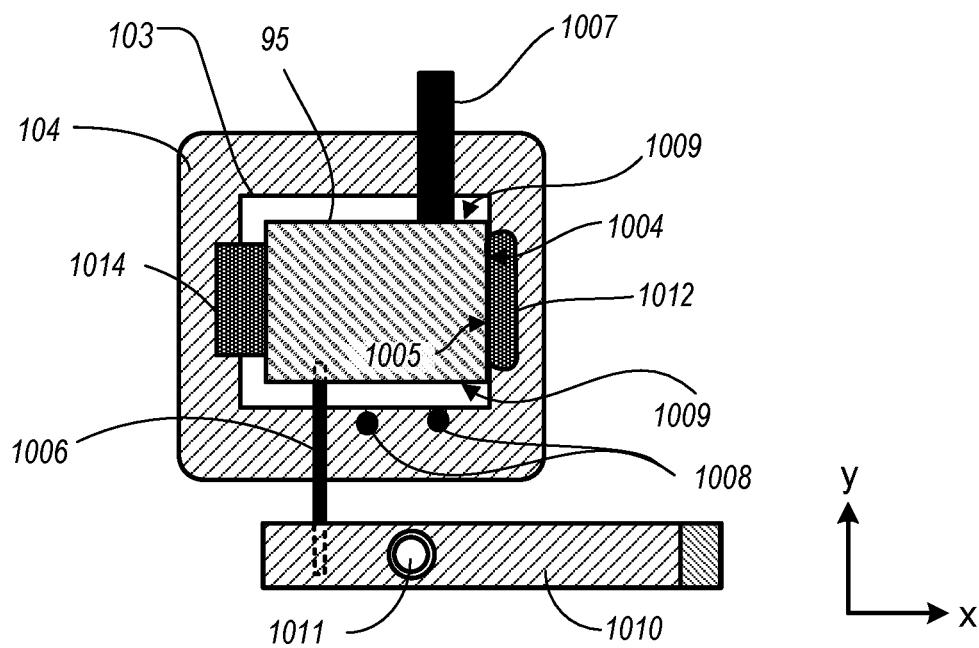

The chamber top 95 can be lowered in various ways as described particularly with respect to various implementations below. In the example illustrated in FIG. 2, the chamber top 95 has a flat bottom surface 200 that is lowered towards the surface 103 such that the surface 200 is kept substantially parallel to the top surface 103 of the sensor 102. As described here, this type of descent is referred to as "linear descent." FIG. 3A illustrates another example where the chamber top 95 is initially positioned at a tilted position such that a first edge of the chamber top 95 is in contact with the surface 103 along a contact line whereas the opposite edge of the chamber top 95 is away from the surface 10. In this configuration, the opposite edge of the chamber top 95 is then lowered along a rotational axis defined by the line of contact between the between the first edge of the chamber top 95 and the surface 103. The chamber top 95 can be lowered at a controlled velocity profile until a point 1006 on the bottom surface of the chamber 95 sits flush with the surface 103. As described here, this type of descent is referred to as a "pivoting descent."

In some instances, data such as positional variables or parameters that control the descent of the chamber top 95 can be selectively chosen based on the type of sample 101 used and then stored for subsequent use. The stored data can then be accessed and automatically applied to a configuration of the system 100 using, for example, a controller. The descent can then be performed with sufficient repeatability for different imaging procedures based on the stored data.

In addition, the descent of the chamber top 95 can be controlled using various mechanisms. For example, the chamber top 95 can be descended manually by a human using physical means (e.g., a circular knob), or automatically with the use of a machine such as an actuator 1010.

In some implementations, after the first edge of the chamber top 95 facing away from the surface 103 is initially descended, corresponding points on the bottom surface of the chamber top 95 come into contact with the sample 101 throughout descent while the opposite end of the chamber top 95 can be raised and lowered repeatedly (e.g., without coming all the way down to a final position). This repeated motion of the chamber top 95 can cause the sample 101 to flow in and out of the space formed between the surface 103 and the chamber top 95, which can be used to produce a mixing effect on the sample 101 to evenly distribute the particles 97 along the surface 103 before an imaging procedure.

In some implementations, the chamber top 95 has a surface 1004 that presses against a surface 1005 of a holder 1012 that assists in the descent of the chamber top 95. The surface 1005 can be formed of encapsulation epoxy deposited on the surface 103 to form the holder 1012. The linear points of contact between the surface 1004 and the surface 1005 can then operate as a hinge for lowering or raising the chamber top 95.

As an example of use, after the sample is deposited onto the surface 103 of the light sensor 102, the chamber top 95 is held up at an angle by another point-of-contact 1006 elsewhere and slid forward until the surface 1004 is pushed against the surface 105 such that it cannot slide further. The hinge then allows the rotational twist of the chamber top 95 along its rotational axis such that the edge of the chamber top 95 opposite to the surface 1004 is lowered towards the surface 103. The chamber top 95 is then slid along the surface 1005 until an adjacent edge of the chamber top 95 hits another barrier 1007 (e.g., either also part of the encapsulation or a separate construction off to the side). This allows the positioning of the chamber top in the y-direction repeatable from test to test (or sample to sample). Then the point of contact 1006 holding up the chamber top is lowered, allowing the chamber top to hinge down until flush with the sensor. In some implementations, the point of contact is lowered in such a way that its friction with the chamber top provides a small force that pushes the chamber top against the ridge, rather than pulling it away, to reduce or avoid disturbance to the position of the chamber top at the wall 1005. It is possible that the chamber top may slide after being placed on (or descended to) the sensor and when the sample is expelled from the chamber. Sometimes guide posts 1008 and/or walls off to the side of the sensor are used to minimize the travelable distance for the chamber top.

In some implementations, the contacting edge 1004 of the chamber top has two extending points at opposite ends 1009 to permit the sample to flow between the points in the direction of the hinge. This may increase uniformity of sample flow in all directions out from under the descending chamber top, reducing artefactual non-uniform distribution of particles 97 (such as cells).

In some instances, the actuator 1010 can be a passive device that is not fixed to the chamber top 95 and is used to lower the chamber top 95. The chamber top 95 may rest on the actuator 1010 and descend via gravity or another force (e.g., magnetism, electromagnetism, a spring). The velocity profile of the descent can be controlled by various means, such as including a rotating counterweight, a dash-pot 1011, magnet, electromagnet, etc.

Although the chamber top 95 is described to descend towards a sensor surface, the mechanisms described can be used with any surface, such as a glass slide, in implementations, such as counting cells or other particles using standard microscopy.

Blood Analysis

A particular group of applications of the system 100 involves analysis of a blood sample. In such applications, the system 100 can be used in detecting and analyzing types of cells in blood (e.g., white blood cells, red blood cells). The system 100 can be used for counting various types of cells, determining normality of blood cells, monitoring blood cell functions, and analyzing blood chemistry.

A. White Blood Cell Concentration and Count Calculations

White blood cells (WBC) are at a relatively low concentration in blood, and the concentration can be further reduced by any dilution added to the blood in preparation of the sample. As a result the total number of white blood cells on the sensor surface to be imaged or counted can be low. Generally, the counting error for particles is the square root of the count, and a low number of particles to be counted may lead to a high percent error.

In some implementations, white blood cell concentration can be increased in a predictable manner. In some implementations, suitable spacer beads can be used such that an average concentration of red blood cells (RBC) can be maintained at a desired level on the sensor surface, while the while blood count is increased. Generally, as the chamber top 95 descends towards the sample, the cells that are in contact with the surface of the chamber top 95 and the surface 103 of the sensor 102 at opposite directions can be trapped. For example, when the cells are being compressed between the opposing surfaces, the cells generally do not move. Accordingly, the size of the spacer beads can be chosen such that the distance between the surfaces of the chamber top and the sensor is less than the average diameter of the white blood cells. In some situations, to maintain the concentration of the red blood cells, the beads can have a diameter larger than the average diameter of the red blood cells. The descending chamber top compresses the white blood cells having a diameter larger than the bead diameter without compressing the red blood cells having an average thickness smaller than the bead diameter. As the total volume of the sample is reduced with the chamber top descending to reach the bead diameter, the concentration of the white blood cells on the sensor surface increases. An example of the bead diameter can be 5 microns. Other suitable diameters can be selected to control the concentration of different cell types in the sample.

Once the chamber top 95 has been lowered to its final height, the height of the chamber (e.g., the height 220 illustrated in FIG. 2) and the surface area of the surface 103 of the sensor 102 can be used to compute the volume of blood imaged on the surface 103. The white blood cell concentration can be increased proportionally with cell size, relative to the concentration of smaller untrapped cells such as red blood cells. The relationship between the size and the concentration of the white blood cells is integrated over all the white blood cell sizes to obtain the average concentration (e.g., the bulk concentration in the sample before the cells are concentrated). This concentration effect can lead to useful improvements in counting statistics.

A wide range of products can be manufactured and delivered based on the architecture and principles that we have discussed. The products could include sensor units, sensor units plus readout units, sensor units plus headboards, sample chambers, chamber tops (or lids), sensor units plus pipettes, sensor units plus pumps, system devices, handheld devices, plugins and attachments to other equipment, pipettes, pre-loaded pipettes, image processors, software, light sources, sample chambers plus light sources plus sensors plus headboards plus electronics in complete devices, and combinations of two or more of these as well as other components.

In considering the wide range of operations performed by the sensors and systems and the broad spectrum of applications, it may be useful to recognize that some relate to imaging, some to analysis, and some to a combination of analysis and imaging.

EXAMPLES

The following examples of implementations of the system 100 use various techniques for sample loading and processing, and/or lowering a chamber top onto a sensor surface for the prior to performing an imaging procedure. As described more particularly below, each implementation provides advantages that can improve an aspect of an imaging procedure.

Example 1—Open Chamber Device

Figure 5A:
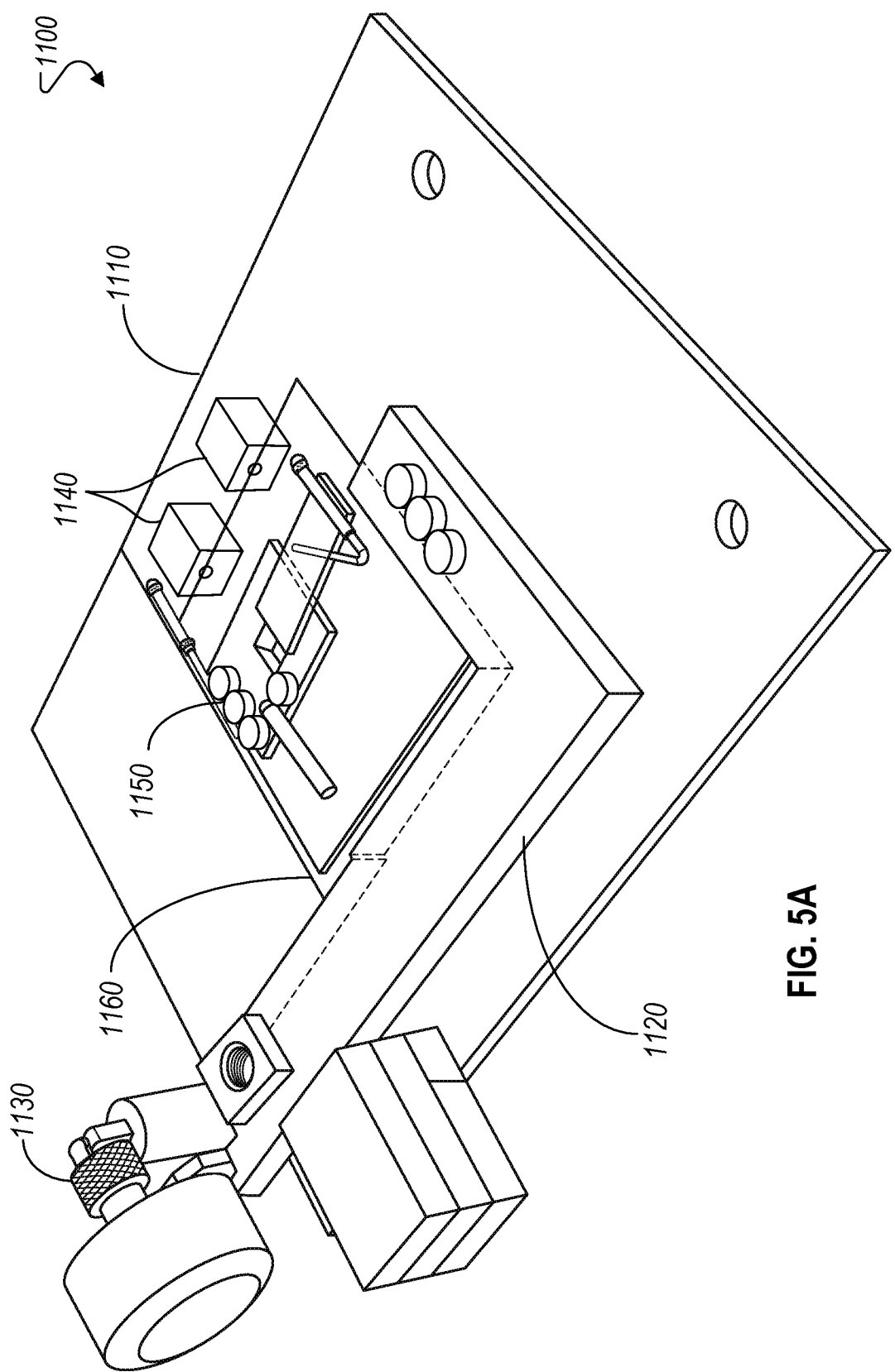
FIGS. 5A-5B are schematic diagrams that illustrate an example of an open chamber contact microscopy system.
Figure 5B:
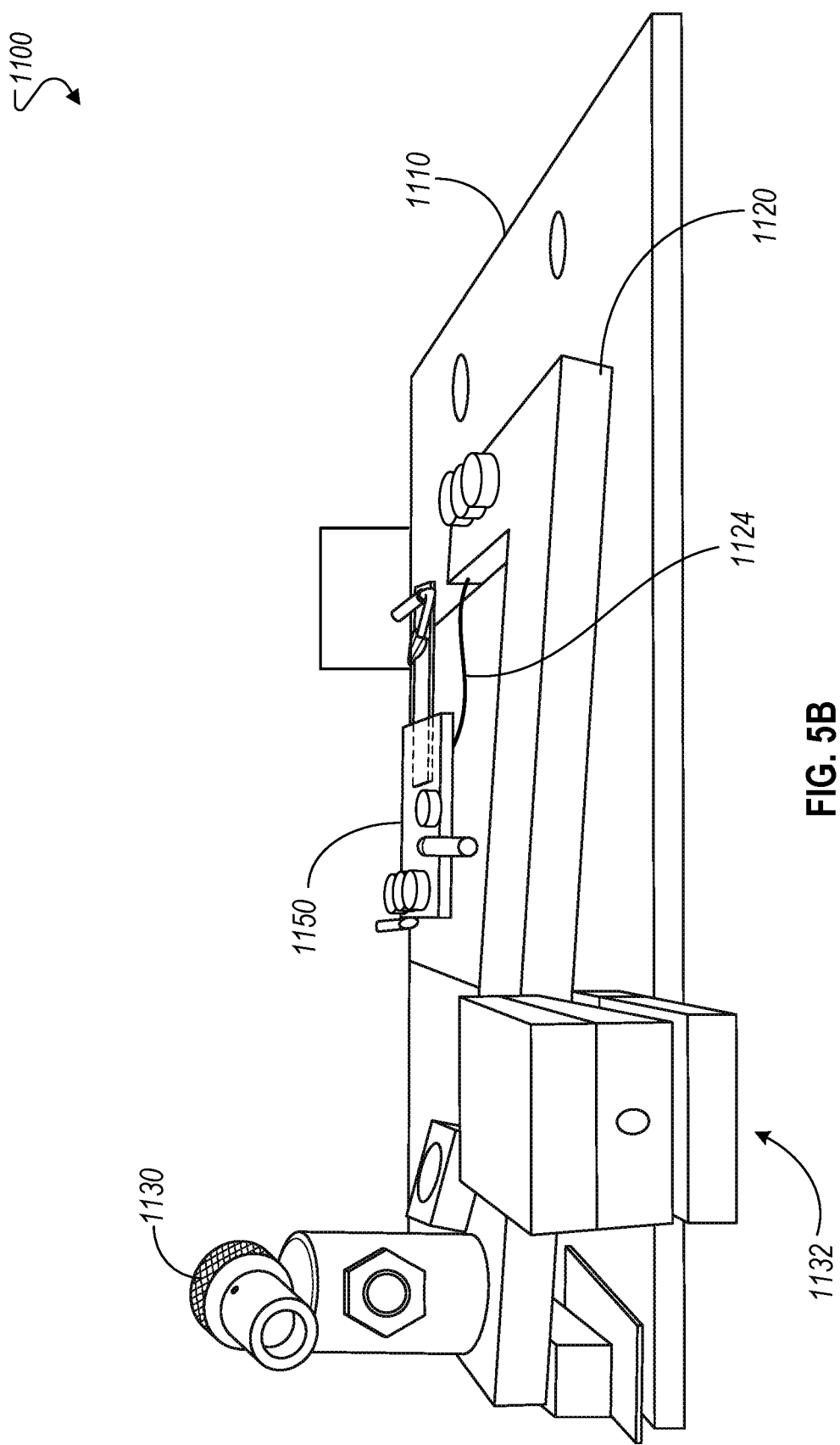

FIGS. 5A-5B illustrate perspective views of an open chamber device 1100 that can be used for performing complete blood counts, as described throughout this disclosure, among other types of tests (e.g., biodosimetry). In this implementation, the chamber top 95 is lowered onto the surface 103 of the light sensor 102 with the use of a carrier arm that is lowered with the use of an actuating element. The chamber top 95 is initially placed on an extension tip of the carrier arm such that the chamber top 95 is not rigidly attached on the carrier arm but loosely attached to enable the chamber top 95 to settles on top of the extension tip of the carrier arm. In addition, the chamber top 95 is placed in such a manner that its descent is in a direction that is substantially parallel to the surface 103 of the light sensor 102.

Referring now to FIGS. 5A and 5B, the system 1100 includes a plate 1110 with an open specimen chamber 1160. The surface of the plate 1110 includes the surface 103 of the light sensor 102, and the headboard 104. A more descriptive view of the open specimen chamber 1160 is illustrated in FIG. 6C. The system 1100 also includes a carrier arm 1120 attached to an actuating device 1130 and support structures 1140 for positioning the chamber top 95 in a substantially parallel manner above the surface 103 prior to operation.

Figure 6A:
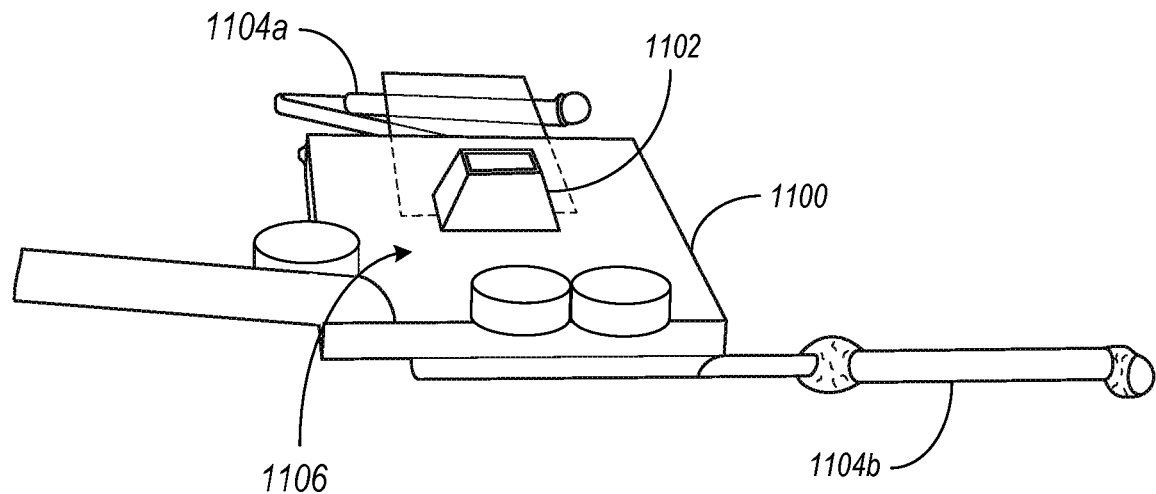
FIGS. 6A-6E are schematic diagrams that illustrate components of the open chamber contact microscopy system.
Figure 6B:
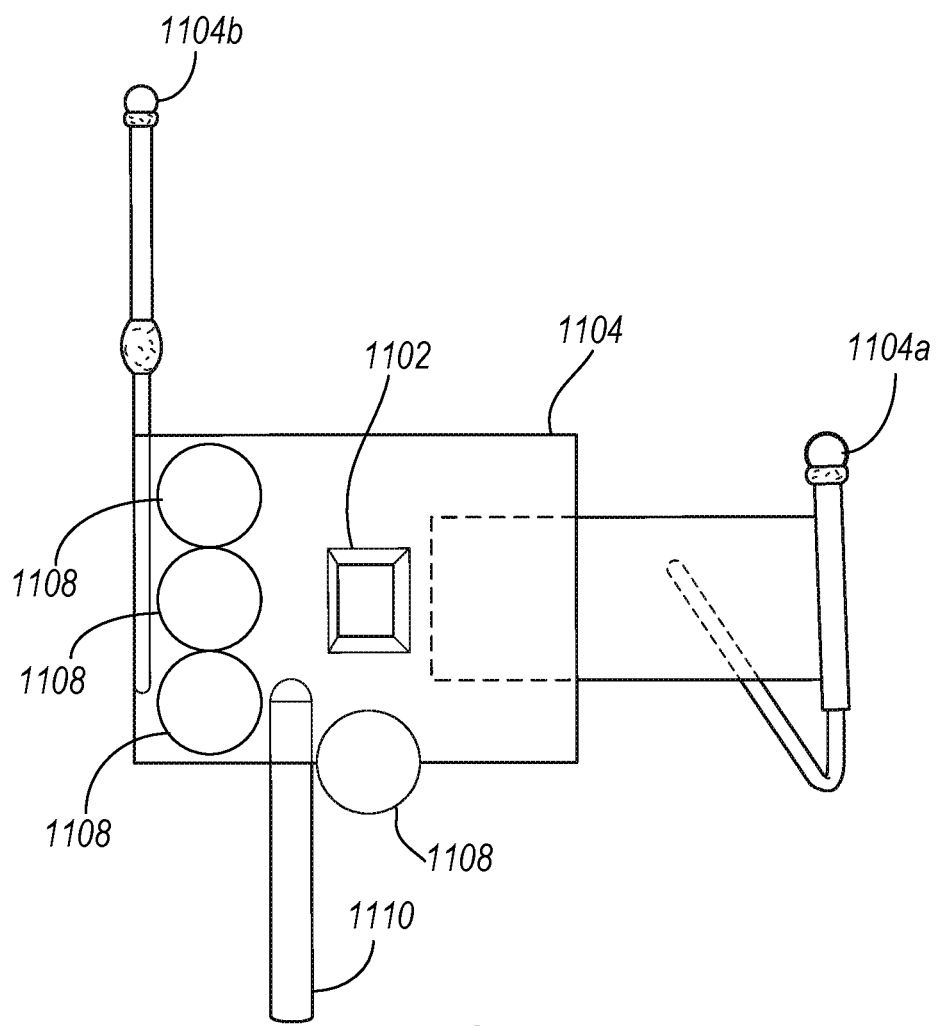
Figure 6C:
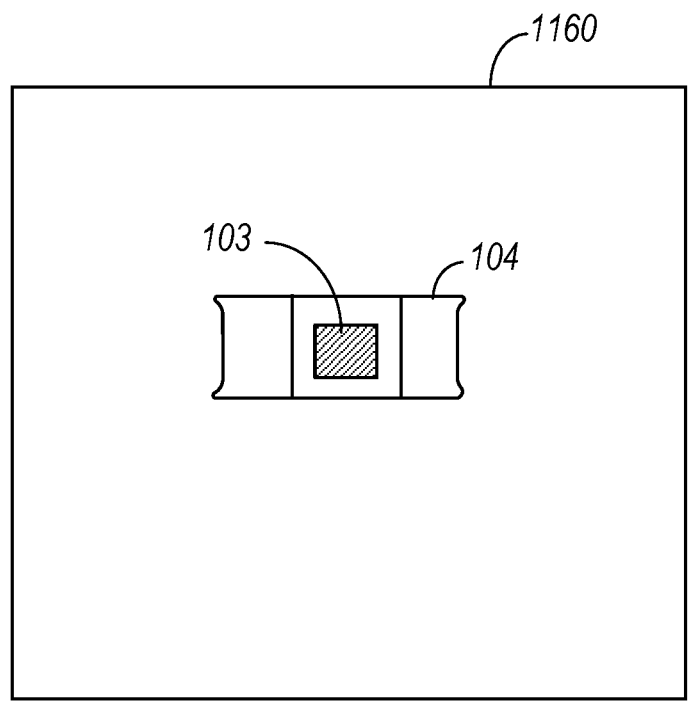
Figure 6D:
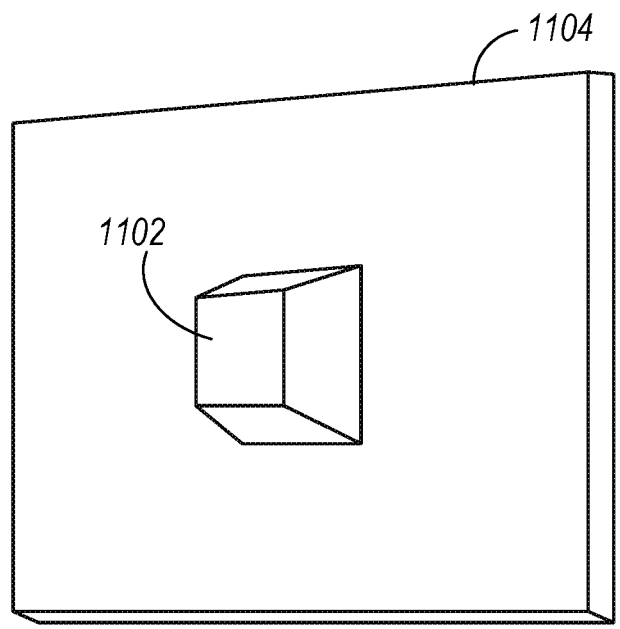
Figure 6E:
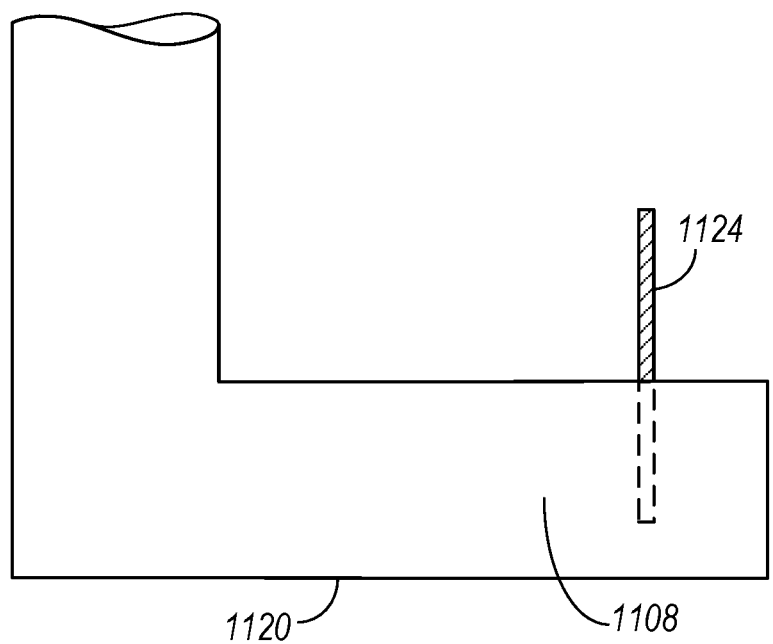

In operation, the chamber top 95 is initially placed above the surface 103 onto an extension of the carrier arm 120 (illustrated as the extension tip 1124 in FIG. 6E). After being placed on the extension tip 1124 of the carrier arm 1120, the chamber top 95 is also positioned parallel to the surface 103 by inserting guiding rods attached to the chamber top 95 (illustrated as guiding rods 1104a and 1104b in FIG. 6B) into apertures on the support structures 1140. The insertion of the guiding rods 1104a, 1104b into the apertures of the support structures 1140 ensures that, as the carrier arm 1020 is lowered, the corresponding descent of the chamber top 95 results in a "linear descent" as described above. A more detailed description of each of the individual components of the system 1100 is provided below.

B. Chamber Top

FIGS. 6A and 6B illustrate a perspective view and a top view, respectively, of the chamber top 95 that is used with the open chamber device 1100. As depicted, the chamber top 95 includes a set of guiding rods 1104a and 1104b that are used to initially position the chamber top 95 onto the extension tip 1124 of the carrier arm 1120 and also ensure that the initial position of the chamber top 95 is substantially parallel to the surface 103.

The chamber top 95 additionally includes a membrane 1104 (illustrated in FIG. 6D) that includes a truncated pyramid member 1102 extending from the bottom surface 1106 (illustrated in FIG. 6A) of the chamber top 95. In operation, as the chamber top 95 is lowered using the carrier arm 1230, the top surface of the truncated pyramid 1102 faces toward the surface 103 as the chamber top 95.

In some instances, the membrane 1104 is a flexible membrane spread across a rigid fame. The membrane is "elastic" in a sense that it capable of deforming as a force is applied toward its surface and then has the ability to conform back to a flat surface after the applied force is removed. For example, the flexible membrane can be used to prevent the application of a rigid force on top of the sample above the surface 103 as the chamber top 95 is lowered. This ensures that the top of the truncated pyramid 1102 pushes down on the sample due only to a gentle, predetermined force to displace the excess volume from the chamber formed between the truncated top of the pyramid 1102 (i.e., the surface that faces the surface 103 of the light sensor 102) and the surface 103 of the light sensor 102.

The top surface of the truncated pyramid member 1102 can be designed such that its surface area corresponds to the surface area 103. In addition, the truncated pyramid member 1102 is composed of a transparent material (e.g., glass, plastic, acrylic, among others) such that light 99 produced by the light source 119 can pass through the truncated pyramid member 1102 and reach the light sensor 102 to collect an image of the volume of the sample 101 placed between the top surface of the truncated pyramid member 1102 and the surface 103 of the light sensor 102.

Although the truncated pyramid member 1102 is described here to be constructed from transparent material (e.g., glass or plastic) to allow for the transmission of light into a sample and then to the light sensor 102, in some implementations, the truncated pyramid member 1102 can be constructed with an opaque material for use in dark field illumination microscopy where only light scattered by the sample is to be detected on the light sensor 102. In other implementations, the top surface of the truncated pyramid member 1102 can also be modified to be transparent only to restricted wavelengths of light with the use of a particular color pigment within the transparent material of the member or on its top or bottom surface, or with the deposition of a thin film spectral filter on the top or bottom surface.

The chamber top 95 may additionally include a set of weighting elements 1108 that evenly distributes the weight along the bottom surface of the chamber top 95 such that the chamber top 95 descends substantially in parallel towards the surface 103 as the carrier arm 1120 is lowered. Although FIG. 8B depicts an example of an arrangement of the weighting elements 1108, in other implementations, the weighting elements 1108 can be positioned in other arrangements so long as the arrangement provides a means to lower the chamber top 95 substantially parallel to the surface 103.

C. Open Specimen Chamber

FIG. 6C illustrates an example of a top view of the open specimen chamber 1160. The open specimen chamber 1160 includes a surface and chip 104 as described previously with respect to FIG. 1.

D. Carrier Arm

FIG. 6E illustrates an example of a top view of the carrier arm 1120. As described here, the carrier arm 1120 includes an extension tip 1124 which freely supports the chamber top 95 in its initial placement. In operation, the actuating device 1130 of the system 1100 is used to manually or automatically lower the height of the carrier arm 1020 relative to the surface 1132 of the base of the system 1100 (as illustrated in FIG. 8B) such that, as the height decreases, the chamber top 95 is lowered towards the surface 103 of the light sensor 102.

The carrier arm 1120 is capable of descending to a height with respect to the open specimen chamber 1160 such that, after a certain height, e.g., at the height of the open specimen chamber 1160 from the base of the system 1100, the chamber top 95 is no longer supported by the extension tip 1124 of the carrier arm 1120 because the top surface of the truncated pyramid member 1102 is in contact with the sample 101 placed on top of the surface 103.

Once the height of the carrier arm 1120 from the surface 1132 of the base is less than the height of the specimen chamber 1160, the chamber top 95 is freely settled on top of surface 103 rather than on the carrier arm 1120, which causes excess volume of the sample 101 placed on top of the surface 103 to flow out of the chamber formed by the top surface of the truncated pyramid member 1102 and the surface 103, as described previously with respect to FIG. 2. In this regard, a gravitational force exerted on the chamber 105 can be used to form a substantially uniformly distributed volume of the sample 101 over the surface 103 without the use of an external force as described here with respect to other implementations.

Example 2—Point-of-Care Device

Figure 7A:
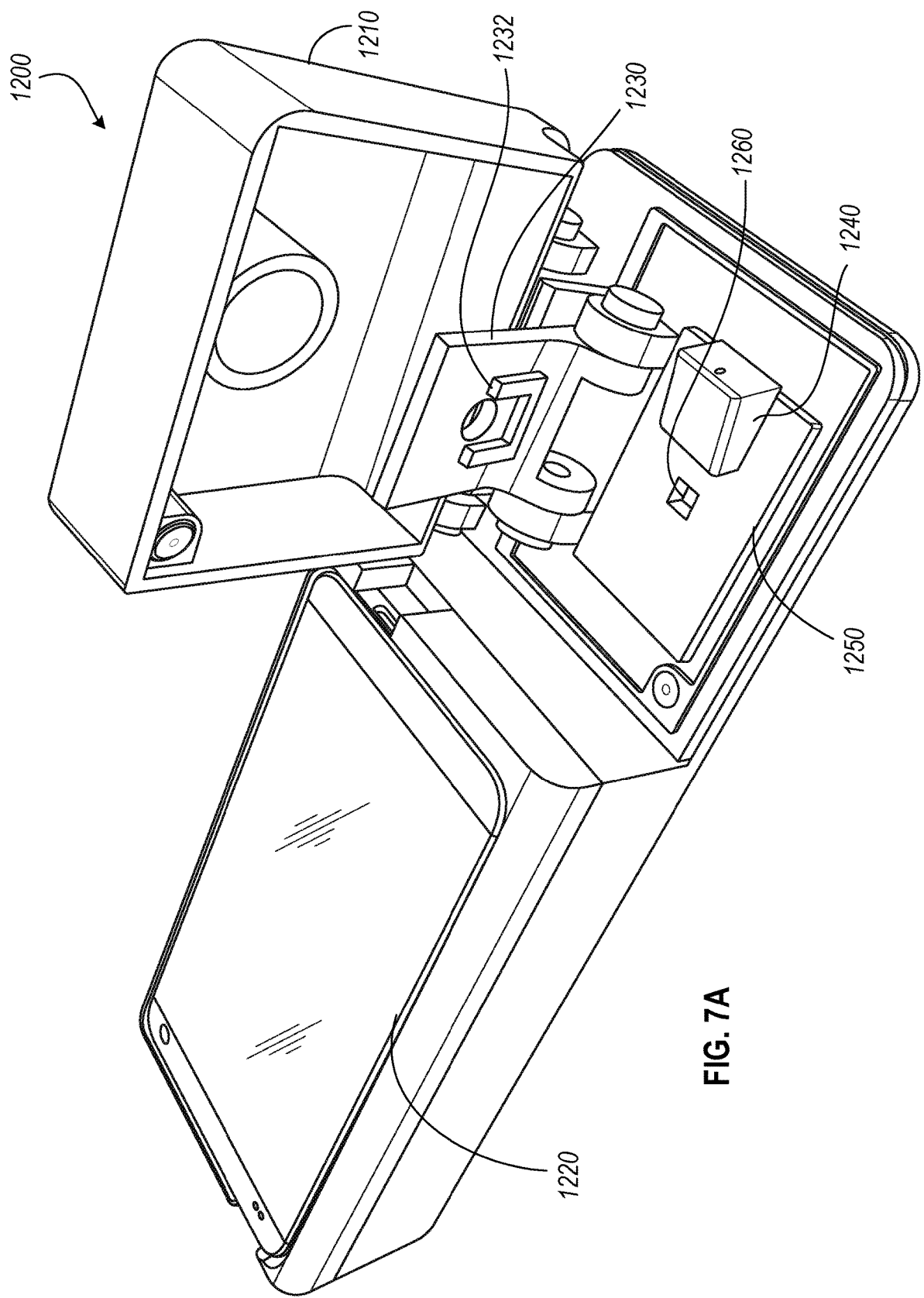
FIGS. 7A-7C are schematic perspective view diagrams that illustrate an example of a point-of-care contact microscopy system.
Figure 7B:
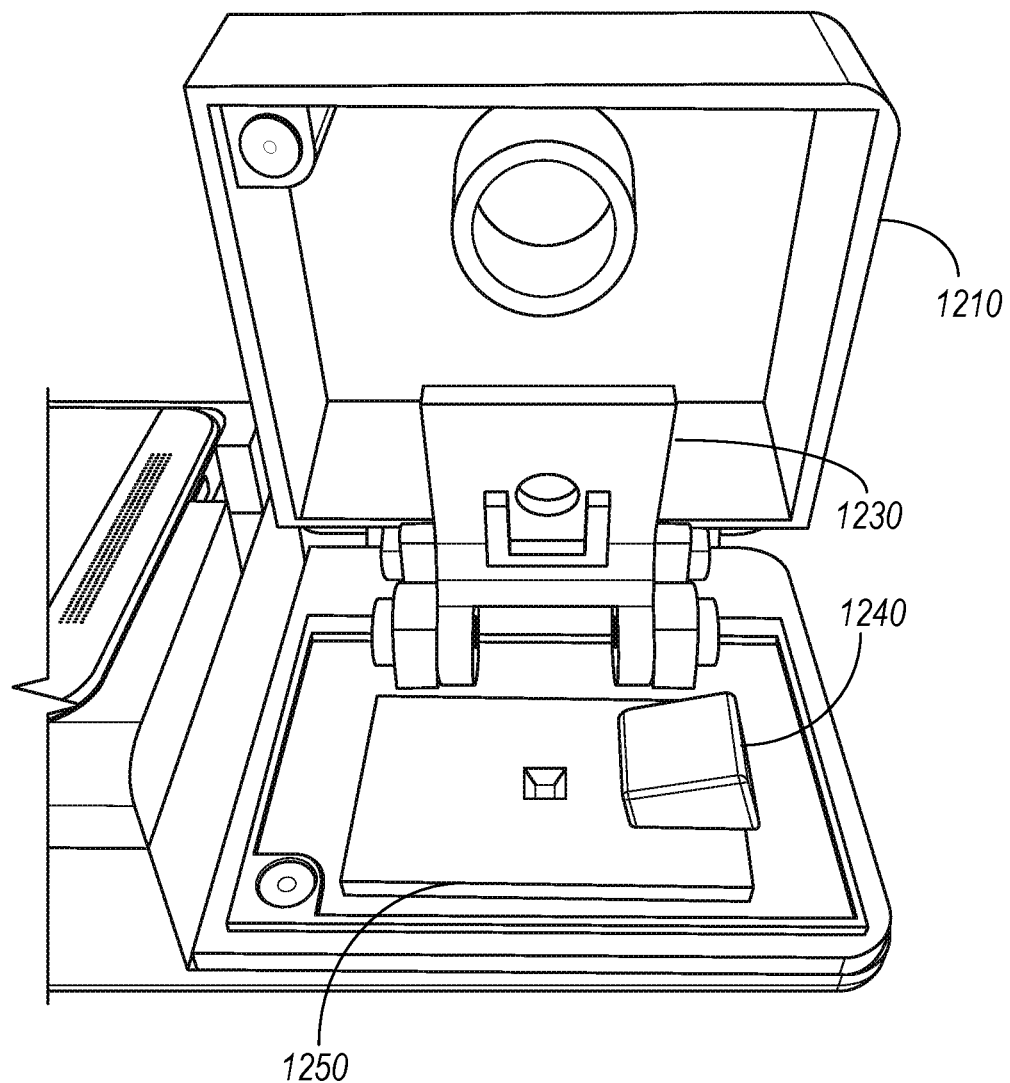
Figure 7C:
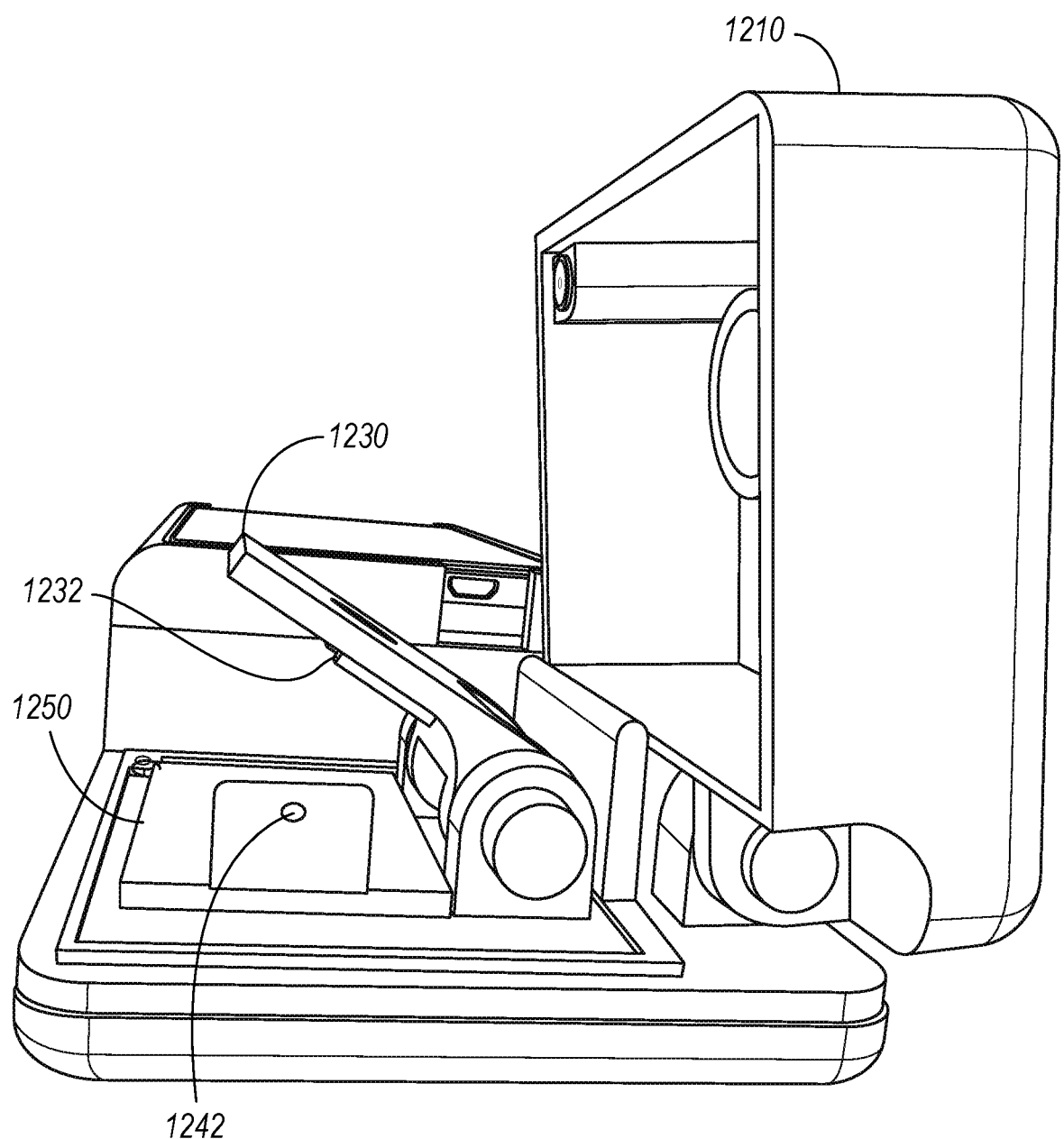
Figure 8:
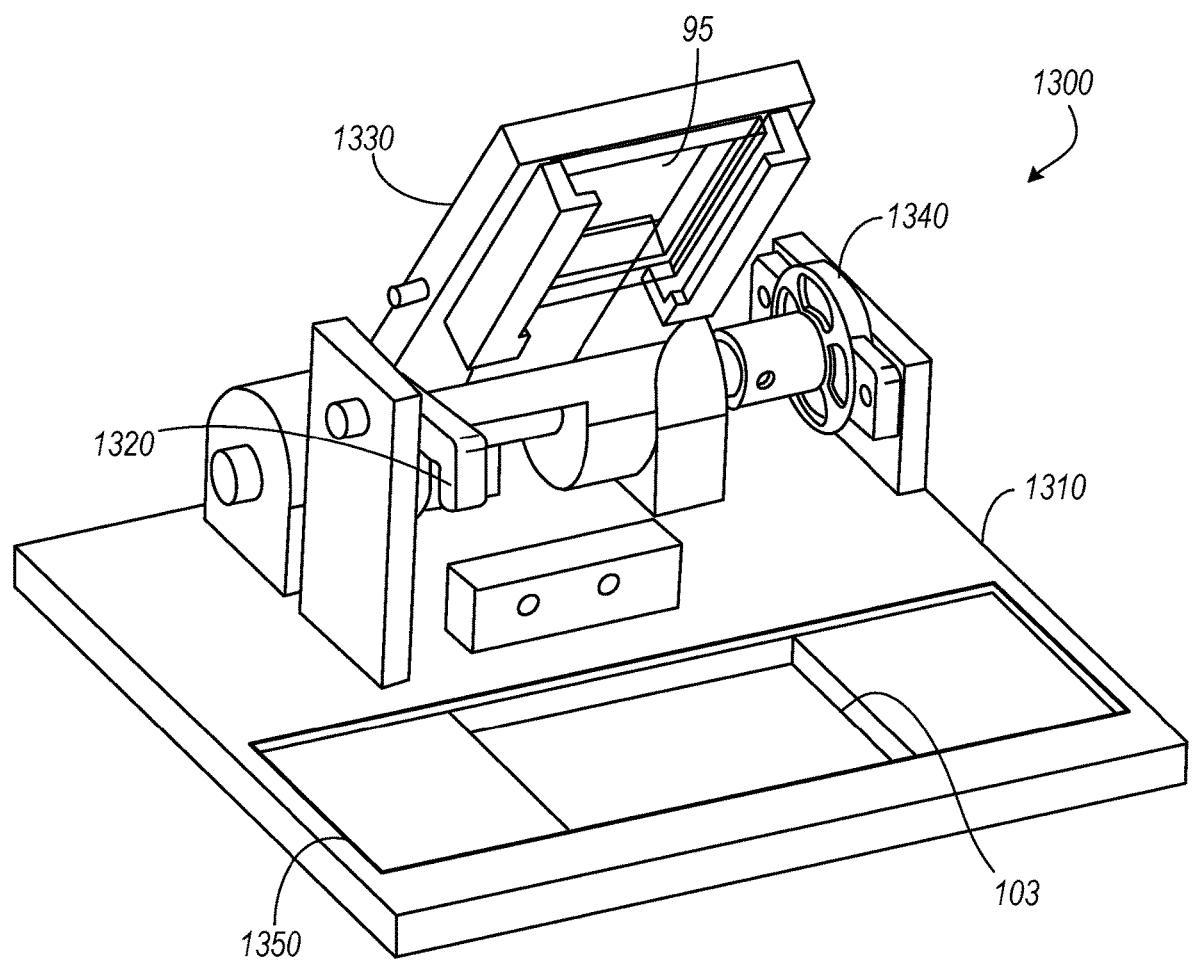
FIG. 8 is a schematic perspective view diagram that illustrates an example of an improved closure mechanism for a contact microscopy system.

FIGS. 7A-7C illustrate perspective views of a point-of-care blood counting device 1200 that can be used in resource-limited regions and/or other areas without access to traditional laboratory benchtop reagents and equipment. In this implementation, the contact microcopy system is housed within a portable housing 1210 that includes a compartment for a mobile device 1220, and a compartment for portable microscopy setup, as described more particularly below. In some instances, the portable microscopy setup can include a more sophisticated setup as illustrated in FIG. 8 that includes a latch mechanism and rotary damper to descend the chamber top 103.

In general, device 1200 is capable of capturing images of a blood sample without the need for any external equipment beyond the sample dispensing apparatus as illustrated in FIGS. 4B-4C. The user device 1220 can be any type of mobile computing device that is capable of performing computing operations and capturing images. In some implementations, the user device 1220 includes software (e.g., a mobile application) that enables a user to capture an image of a blood sample without significant training or sample preparation.

In some instances, the device 1200 can be used in resource-limited regions in the developing world where the operator that performing a blood count test lacks the training necessary to perform a blood count using traditional microscopic techniques. In such instances, the device 1200 can be used to provide a low ease-of-use, portable means to accurately provide a blood count with limited sample preparation and processing. For instance, the user device 1220 can provide an interface that enables the operator to dispense a volume of the sample 110 into the portable microscopy setup, and then capture an image of the dispensed blood by providing a simple user input on the user device 1220. Particular descriptions related to the components of the portable microscopy setup are provided in greater detail below.

A. Portable Microscopy Setup

FIGS. 7A-7C illustrate various views of device 1200 including a compartment for housing the portable microscopy setup. The setup includes a carrier arm 1230, a slot 1232 to hold the chamber top, a headboard 1250 with a sample recess 1260, and a sample delivery module 1240 with pipette aperture 1242. The chamber top 95 can be attached and/or configured to the carrier arm 1230 in a variety of configurations. In some instances, the chamber top 95 is a separable component that includes a truncated pyramid 1102 depicted in FIG. 6D) In addition, the device 1200 further includes a light source that is place directly above the carrier arm 1230 (and the chamber top 95) when the lid of the housing 1210 is the closed position, and a sensor (not shown) such as the light sensor 102 at the bottom of the sample recess 1260.

In operation, the initial configuration of the carrier arm 1230 faces upward to enable an operator to prepare the device 1200 for an imaging operation as illustrated in FIG. 7B A chamber top 95 is inserted into the slot 1232 in the carrier arm 1230 such that the top surface 1102 of the truncated pyramid will, when the carrier arm is fully descended, face the surface 103 inside the sample recess 1240. A volume of a sample can then be introduced into the sample recess 1260 using a pipette and inserting the tip of the pipette through the aperture 1242 of the sample delivery module 1240 as illustrated in FIG. 7C. The dimensions of the aperture 1242 can configured for use with a specific type of pipette used, and for the volume of sample to be dispensed into the sample recess 1260. For instance, the aperture 1242 can be larger for larger-sized pipettes so that when the corresponding pipette is inserted into the sample aperture 1242, the tip of the pipette that dispenses the volume of the sample is above the center point of the sample recess 1260. In some instances, the sample delivery module 1240 may be interchangeable such that a single device 1200 can be used with different types of pipettes.

Once the volume of the sample is dispensed into the sample recess 1260, the carrier arm 1230 is then descended towards the headboard 1250. For instance, as the carrier arm 1230 with the chamber top 95 descends towards the headboard 1250, coming to a stop at a position, set by the thickness of the slot feature 1232, where the chamber top 95 is resting on the spacing features 230, no longer supported by the lower flanges of the slot 1232. In this configuration, after the carrier arm 1230 is descended to its final position, as described above, the top surface of the truncated pyramid can then press on volume of the sample dispensed in the sample recess 1260 such that the excess sample volume flows out of the chamber defined by the top surface of the truncated pyramid 1102 and the surface 103, as described previously, with respect to the Open Chamber Device Once the carrier arm and the chamber top 95 is in this position, the lid of the housing 1210 can then be closed to exclude extraneous light and an image of the sample can be captured using the user device 1220 as a controller for the light sensor 102 beneath the sample recess 1260.

B. Improved Closure Mechanism Apparatus

In some implementations, the portable microscopy setup of the device 1200 includes an improved closure mechanism apparatus 1300 illustrated in FIG. 8. The apparatus 1300 is similar to that of the device 1200 depicted in FIGS. 7A-7C, but includes additional mechanical components (e.g., a latch mechanism 1320, a spring (not shown) to drive descent of the carrier arm once the latch is released, and a rotary damper 1340 to regulate the rate of carrier arm descent) to more effectively lower a carrier arm 1330 on to the surface 103 to accurately place the truncated pyramid of the chamber top 95 onto the surface 103 of the light sensor 102 within the sample aperture 1240. In this regard, the apparatus 1300 can be implemented into the device 1200 to improve ease-of-use (e.g., reducing the need to manually lower the carrier arm 1230 in a specific manner) and reduce result variability between subsequent imaging procedures.

Example 3—Closed Chamber Device

FIGS. 9A-9D illustrate different views of a closed chamber device 1400 for performing complete blood counts, as described throughout this disclosure, among other types of tests. Compared to the open chamber device 1100 described previously, the closed chamber device 1400 reduces the need to manually load or remove a sample onto or from the surface 103 and encloses the sample such that the operator is not exposed to potentially harmful components of the sample. In addition, the device 1400 enables automatic cleaning of the surface 103 by injecting a volume of a cleaning reagent into the closed chamber.

C. System Components

The closed chamber device 1440 includes a headboard 1410 attached to an enclosing body 1420 with a set of rigid walls 1430 permanently bonded to the headboard 410 and the enclosing body 1420. The enclosing body 1420 can be any type of suitably transparent rigid material such as glass, acrylic, plastic, etc., that enables transmission of light from a light source above the enclosing body 1420 in the enclosed space within the rigid sidewalls 1430, which is described more particularly below. The headboard 1410 may be an integrated circuit board that includes a light sensitive sensor such as the light sensor 102 with a surface 103 that is exposed to a sample fluid during an imaging operation.

Figure 9A:
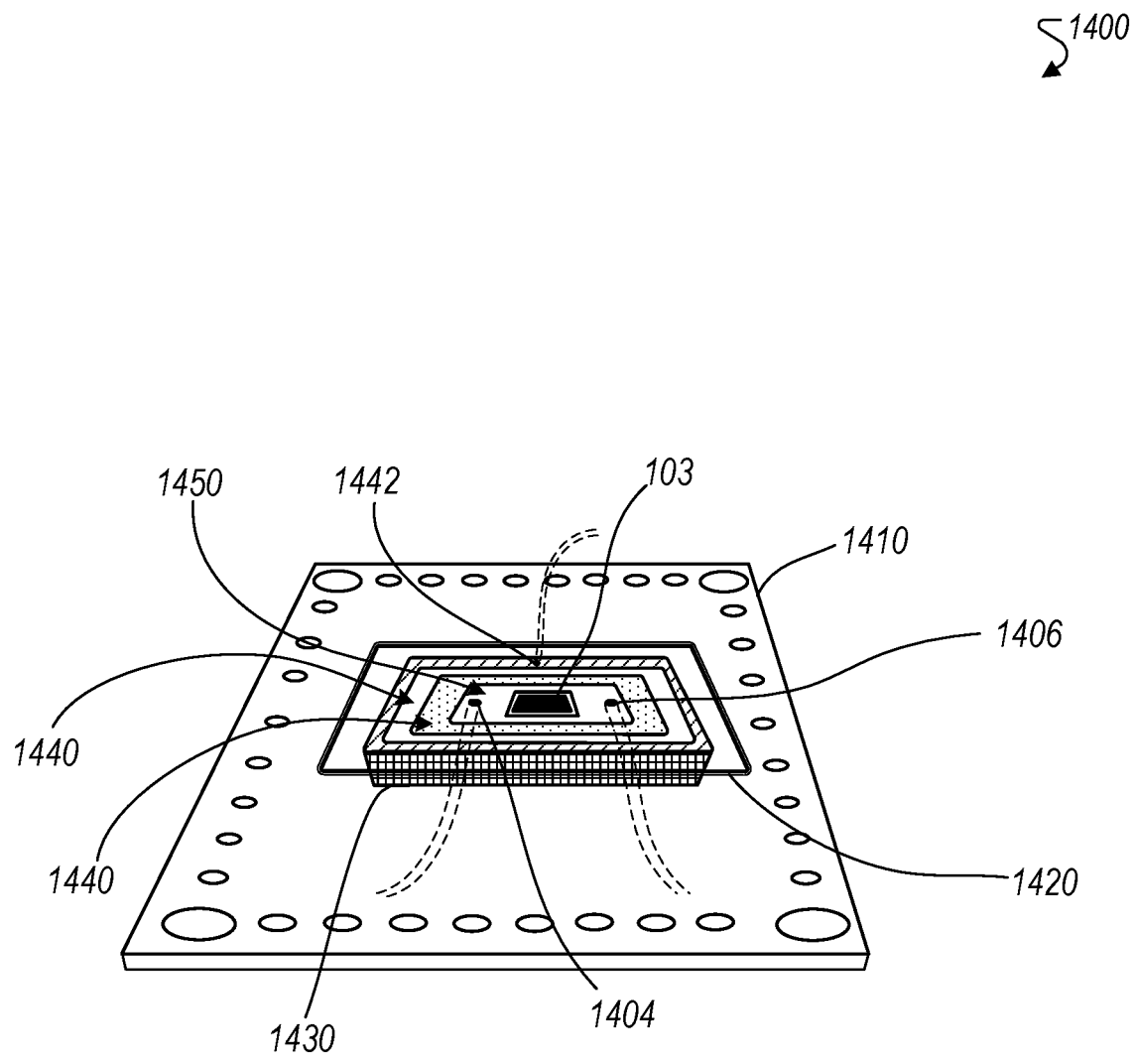
FIGS. 9A-9D illustrates schematic diagrams that illustrate an example of a closed chamber contact microscopy system.
Figure 9B:
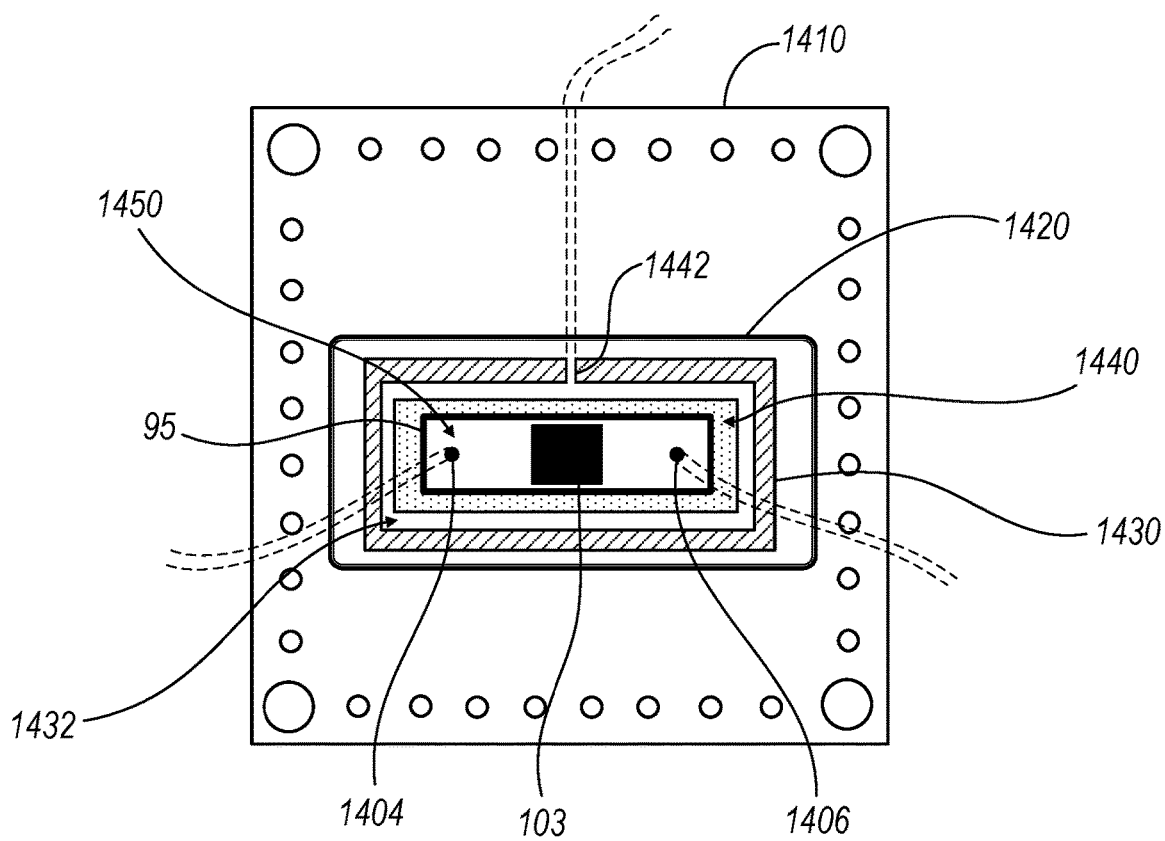
Figure 9C:
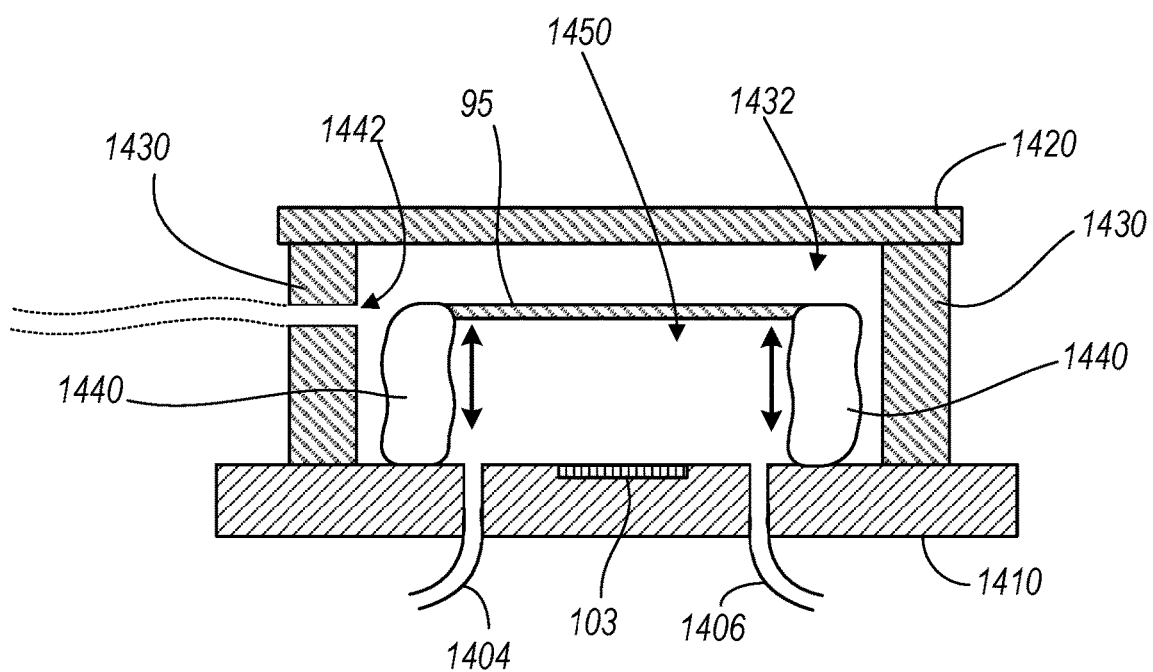

FIGS. 9B and 9C illustrate a top view and cross-sectional view, respectively. Once the enclosing body headboard 1410, the rigid sidewalls 1430 and the enclosing body 1420 are permanently bonded together, an enclosed space is formed within the rigid sidewalls 1430. The outer portion of the enclosed space within the rigid sidewalls 1430 includes a pressure chamber 1432 where positive or negative pressure may be applied through the aperture 1442 on the rigid sidewalls 1430. The aperture 1442 can be placed on any of the rigid walls so long as the application of negative and positive pressure can be uniformly distributed throughout the entire volume of the pressure chamber 1432.

The pressure chamber 1432 surrounds a set of deformable sidewalls 1440 enclosing a fluid chamber 1450. The deformable sidewalls 1440 can be made of any suitable solid material that withstands the applied pressure within the pressure chamber 1432. In some instances, the deformable sidewalls 1440 may be made of a solid elastomer that is capable of deforming as a result of the applied pressure to the pressure chamber 1432. The chamber top 95 of the fluid chamber 1450 is a transparent solid or rigid material that allows for the passage of light from a light source into the fluid chamber 1450. The chamber top 95 is rigid such that any pressure applied to the pressure chamber 1432 does not cause it to deformation, preserving its smooth flat surface facing the surface 103 of the light sensor 102. The chamber top 95 is affixed to the deformable side walls 1440 to allow for varying heights of the fluid chamber 1450 as a result of the negative or positive pressure applied to the pressure chamber 1432, as described more particularly below.

D. Operation

Figure 9D:
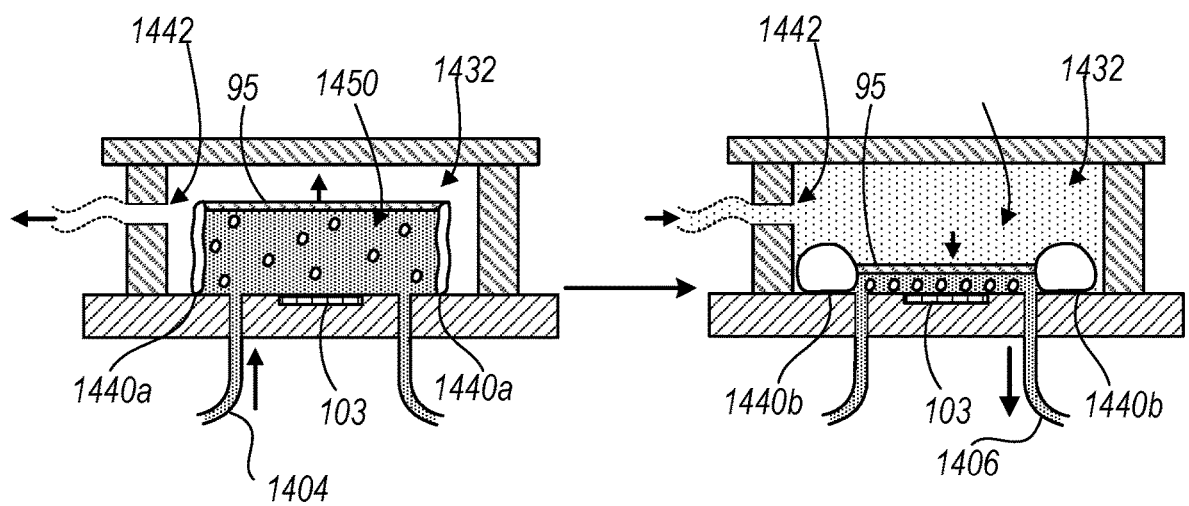

FIG. 9D illustrates an example of operating the closed chamber device 1440 prior to performing an imaging procedure. As described previously, sample fluid to be analyzed enters the fluid chamber 1450 through the inlet port 1404 and exits the fluid chamber 1450 through the outlet port 1406. In an initial state, the height of the fluid chamber 1450 is increased to enable the injection of sample fluid into the fluid chamber 1450 (e.g., shown on the left side of FIG. 9D). This is accomplished by generating a pressure differential between the pressure chamber 1432 and the fluid chamber 1450 by applying a negative pressure to the pressure chamber 1432. In some instances, the negative pressure may be provided by applying a suction force through the aperture 1442 to withdraw a volume of liquid or gas contained within the pressure chamber 1432. The difference in pressure between the pressure chamber 1432 and the fluid chamber 1450 causes the deformable sidewalls 1440 to deform to a state 1440a to accommodate the volume of sample fluid that enters into the fluid chamber 1450, resulting in an increase to the height of the fluid chamber 1450.

Once the appropriate sample volume is delivered in the fluid chamber 1450, the chamber top 95 may be lowered towards the surface 103 to generate a cellular monolayer of particles as described throughout this specification. This can be accomplished by applying a positive pressure to the pressure chamber 1432 such that the positive pressure deforms the deformable sidewalls 1440 to a state 1440b to accommodate the increased pressure within the pressure chamber. In some instances, the positive pressure may be providing by applying a volume of gas or transparent liquid into to the pressure chamber to displace the deformable sidewalls 1440 and consequently lower the chamber top 95 toward the surface 103. As the height of the fluid chamber 1450 is reduced, the excess volume of the sample fluid within the fluid chamber exits the fluid chamber 1450 through the outlet port 1406. After the chamber top 95 reaches its final height, e.g., (set by the spacing features 230 described previously with respect to FIG. 2) an image of the remaining fluid sample within the fluid chamber 1450 can be captured.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

A wide range of products can be manufactured and delivered based on the architecture and principles that we have discussed. The products could include sensor units, sensor units plus readout units, sensor units plus headboards, sample chambers, chamber tops (or lids), sensor units plus pipettes, sensor units plus pumps, system devices, handheld devices, plugins and attachments to other equipment, pipettes, pre-loaded pipettes, image processors, software, light sources, sample chambers plus light sources plus sensors plus headboards plus electronics in complete devices, and combinations of two or more of these as well as other components.

In considering the wide range of operations performed by the sensors and systems and the broad spectrum of applications, it may be useful to recognize that some relate to imaging, some to analysis, and some to a combination of analysis and imaging.

Other embodiments are within the scope of the following claims and other claims.

What is claimed is:

1. An apparatus comprising:
   a solid member;
   a light sensitive imaging sensor;
   a deformable member coupling the solid member to a surface having the light sensitive imaging sensor, the deformable member comprising side walls enclosing a fluid chamber configured to receive a volume of fluid; and
   a pressurizable chamber distinct from the fluid chamber and enclosing a liquid or gas impinging on an exterior of the fluid chamber, the pressurizable chamber configured to deform the deformable member to cause adjustment to a height of the fluid chamber.

2. The apparatus of claim 1, wherein a surface of the light sensitive imaging sensor comprises a hydrophilic coating.

3. The apparatus of claim 1, wherein a surface of the solid member comprises a hydrophilic coating.

4. The apparatus of claim 1, further comprising a sample delivery component for preparing and delivering the fluid to the fluid chamber.

5. The apparatus of claim 4, wherein the sample delivery component comprises at least two volumetric capillary tubes, a nozzle for mixing fluids within the at least two volumetric capillary tubes, and an output tip through which the fluid is delivered to the fluid chamber.

6. The apparatus of claim 1, wherein the solid member permits passage of light into the fluid chamber.

7. The apparatus of claim 1, wherein the pressurizable chamber encloses the fluid chamber and has a transparent roof.

8. The apparatus of claim 7, wherein the pressurizable chamber comprises an aperture configured to receive an application of pressure.

9. The apparatus of claim 8, wherein the aperture, the pressurizable chamber, and the fluid chamber are configured so that a pressure applied through the aperture is uniformly distributed throughout the entire volume of the pressurizable chamber.

10. The apparatus of claim 1, wherein a base of the fluid chamber comprises an integrated circuit board.

11. The apparatus of claim 1, further comprising
    a device coupler to couple electronically to a mobile device capable of accepting electronic communications corresponding to signals derived from the light sensitive imaging sensors, and
    a housing to hold the solid member, the light sensitive imaging sensor, the deformable member, the pressurizable chamber, and the device coupler.

12. The system of claim 11, wherein the surface of the light sensitive imaging sensor to receive the fluid sample comprises a hydrophilic coating.

13. The system of claim 11, wherein the surface of the body to touch a portion of the fluid sample comprises a hydrophilic coating.

14. The system of claim 11, further comprising a sample delivery component for preparing and delivering the fluid sample to the surface of the light sensitive imaging sensor.

15. The system of claim 11, wherein the sample delivery component comprises at least two volumetric capillary tubes, a nozzle for mixing fluids within the at least two volumetric capillary tubes, and an output tip through which the fluid sample is delivered to the surface of the light sensitive imaging sensor.

16. The system of claim 11, wherein the surface of the body to touch the portion of the fluid sample is on a component that is separable from the body.

17. The apparatus of claim 11, wherein the electronic communications exchanged between the mobile device and the light sensitive imaging sensor comprise an instruction to capture an image of a portion of the fluid placed on the surface of the light sensitive imaging sensor.

18. The apparatus of claim 1, wherein the solid member comprises a plate and a protruding element.

19. The apparatus of claim 18, wherein:
    dimensions of a surface of the protruding element are identical to dimensions of the surface of the light sensitive imaging sensor.

20. The apparatus of claim 18, wherein the shape of the protruding element comprises a truncated pyramid.

21. The apparatus of claim 1, wherein the fluid chamber comprises an inlet port and an outlet port.

22. The apparatus of claim 21, wherein the fluid chamber and the inlet port are configured so that an increase in the height of the fluid chamber allows fluid to flow into the fluid chamber.

23. The apparatus of claim 21, wherein the fluid chamber and the outlet port are configured so that a decrease in the height of the fluid chamber causes fluid to flow out of the fluid chamber.

24. The apparatus of claim 1, wherein the solid member comprises a flat surface facing the surface of the light sensitive imaging sensor.

25. The apparatus of claim 1, wherein the light sensitive imaging sensor is fixed in position and the deformable member allows the solid member to be moved in reference to the light sensitive imaging sensor.

26. The apparatus of claim 1, wherein the deformable member and the solid member are configured to maintain a surface of the solid member parallel to a surface of the light sensitive imaging sensor.

27. The apparatus of claim 1, further comprising spacing features that define a minimum height of the fluid chamber.

28. The apparatus of claim 27, wherein the spacing features comprise microspheres.

29. The apparatus of claim 27, wherein the spacing features are dispersed within the volume of fluid.

30. A method comprising:
- injecting a fluid sample into a fluid chamber;
- adjusting a volume of liquid or gas into a pressurizable chamber distinct from the fluid chamber, the volume of fluid or gas impinging against an exterior of the fluid chamber to deform a deformable member to reduce a volume of the fluid chamber to cause a reduction of volume of the sample; and
- after reducing the volume of the sample, capturing an image of the sample at a light-sensitive sensor surface within the fluid chamber.

31. The method of claim 30, further comprising adjusting a volume of liquid or gas impinging against an exterior of the fluid chamber to deform the deformable member to increase the volume of the fluid chamber.

32. The method of claim 31, wherein deforming the deformable member to increase the volume of the fluid chamber comprises withdrawing a volume of liquid or gas contained within a pressurizable chamber enclosing the fluid chamber.

33. The method of claim 30, wherein the pressurizable chamber encloses the fluid chamber.

34. The method of claim 30, wherein reducing the volume of the fluid chamber comprises reducing a height of the fluid chamber to allow only a monolayer of the sample to remain in the chamber.

35. The method of claim 30, further comprising cleaning the fluid chamber by injecting a cleaning fluid into the fluid chamber.

36. The method of claim 30, wherein the sample comprises blood.

37. The method of claim 36, further comprising performing a blood count of the sample.

* * * * *

UNITED STATES PATENT AND TRADEMARK OFFICE
CERTIFICATE OF CORRECTION

PATENT NO. : 10,606,059 B2
APPLICATION NO. : 16/404633
DATED : March 31, 2020
INVENTOR(S) : Alan Marc Fine Page 1 of 1

It is certified that error appears in the above-identified patent and that said Letters Patent is hereby corrected as shown below:

In the Specification

Column 1, Line 23 please delete "entireties," and insert --entireties.-- therefor.

In the Claims

Column 22, in Claims 12-16 please delete "system" and insert --apparatus-- therefor.

Signed and Sealed this
Thirtieth Day of June, 2020

Andrei Iancu
*Director of the United States Patent and Trademark Office*